(12) United States Patent
Conca et al.

(10) Patent No.: US 10,765,672 B2
(45) Date of Patent: Sep. 8, 2020

(54) PHARMACEUTICAL FORMULATIONS OF A HIF HYDROXYLASE INHIBITOR

(71) Applicant: FibroGen, Inc., San Francisco, CA (US)

(72) Inventors: David Conca, San Francisco, CA (US); Lee Allen Flippin, Woodside, CA (US); Scott David Leigh, Castro Valley, CA (US); Claudia Witschi, San Francisco, CA (US); Lee Robert Wright, Redwood City, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 16/035,503

(22) Filed: Jul. 13, 2018

(65) Prior Publication Data

US 2019/0008846 A1    Jan. 10, 2019

Related U.S. Application Data

(63) Continuation of application No. 14/896,353, filed as application No. PCT/US2014/041021 on Jun. 5, 2014, now abandoned.

(Continued)

(51) Int. Cl.
*A61K 31/472* (2006.01)
*A61K 9/28* (2006.01)
(Continued)

(52) U.S. Cl.
CPC .......... *A61K 31/472* (2013.01); *A61K 9/2009* (2013.01); *A61K 9/282* (2013.01);
(Continued)

(58) Field of Classification Search
CPC .... A61P 9/00; A61P 43/00; A61P 7/06; A61P 9/10; A61K 9/4816; A61K 9/4883; A61K 9/282; A61K 9/2813; A61K 9/485; A61K 9/4891; A61K 9/2009; A61K 9/4858; A61K 9/2013; A61K 9/2027; A61K 9/2054; A61K 9/2018; A61K 9/4825; A61K 31/472
See application file for complete search history.

(56) References Cited

U.S. PATENT DOCUMENTS 6,093,730 A    7/2000 Weidmann et al.
7,060,707 B2   6/2006 Wiesner et al.
(Continued)

FOREIGN PATENT DOCUMENTS

EP    0650961    5/1995
EP    0911340    4/1999
(Continued)

OTHER PUBLICATIONS

10% Papaverine Hydrochloride Powd. "Mylan", Medicament interview form, Jan. 2013.
(Continued)

*Primary Examiner* — Blessing M Fubara
(74) *Attorney, Agent, or Firm* — Leanne C. Price; Sheppard Mullin Richter & Hampton LLP

(57) ABSTRACT

The present disclosure relates to pharmaceutical formulations of [(4-hydroxy-1-methyl-7-phenoxy-isoquinoline-3-carbonyl)-amino]-acetic acid and methods of use thereof.

6 Claims, 6 Drawing Sheets

Related U.S. Application Data

(60) Provisional application No. 61/831,909, filed on Jun. 6, 2013.

(51) Int. Cl.
*A61K 9/48* (2006.01)
*A61K 9/20* (2006.01)

(52) U.S. Cl.
CPC ............ *A61K 9/2813* (2013.01); *A61K 9/485* (2013.01); *A61K 9/4816* (2013.01); *A61K 9/4858* (2013.01); *A61K 9/4883* (2013.01); *A61K 9/4891* (2013.01); *A61K 9/2013* (2013.01); *A61K 9/2018* (2013.01); *A61K 9/2027* (2013.01); *A61K 9/2054* (2013.01); *A61K 9/4825* (2013.01)

(56) References Cited

U.S. PATENT DOCUMENTS

| | | |
|---|---|---|
| 7,323,475 B2 | 1/2008 | Arend et al. |
| 7,629,357 B2 | 12/2009 | Arend et al. |
| 7,696,223 B2 | 4/2010 | Deng et al. |
| 7,863,292 B2 | 1/2011 | Arend et al. |
| 7,928,120 B2 | 4/2011 | Arend et al. |
| 8,017,625 B2 | 9/2011 | Arend et al. |
| 8,168,221 B2 | 5/2012 | Blyth et al. |
| 8,217,043 B2 | 7/2012 | Deng et al. |
| 8,269,008 B2 | 9/2012 | Arend et al. |
| 8,278,325 B2 | 10/2012 | Arend et al. |
| 8,324,405 B2 | 12/2012 | Ho et al. |
| 8,426,451 B2 | 4/2013 | Yokoe et al. |
| 8,703,795 B2 | 4/2014 | Turtle et al. |
| 8,759,373 B2 | 6/2014 | Arend et al. |
| 8,765,956 B2 | 7/2014 | Arend et al. |
| 8,883,823 B2 | 11/2014 | Witschi et al. |
| 8,916,585 B2 | 12/2014 | Arend et al. |
| 8,921,389 B2 | 12/2014 | Ng et al. |
| 8,927,591 B2 | 1/2015 | Ho et al. |
| 8,952,160 B2 | 2/2015 | Zhou et al. |
| 9,000,006 B2 | 4/2015 | Turtle et al. |
| 9,115,085 B2 | 8/2015 | Witschi et al. |
| 9,149,476 B2 | 10/2015 | Ho et al. |
| 9,174,976 B2 | 11/2015 | Arend et al. |
| 9,271,970 B2 | 3/2016 | Ng et al. |
| 9,339,527 B2 | 5/2016 | Arend et al. |
| 9,340,511 B2 | 5/2016 | Thompson et al. |
| 9,371,288 B2 | 6/2016 | Witschi et al. |
| 9,387,200 B2 | 7/2016 | Zhou et al. |
| 9,409,892 B2 | 8/2016 | Ho et al. |
| 9,617,218 B2 | 4/2017 | Witschi et al. |
| 9,643,928 B2 | 5/2017 | Witschi et al. |
| 9,695,170 B2 | 7/2017 | Ng et al. |
| 9,708,269 B2 | 7/2017 | Thompson et al. |
| 9,918,977 B2 | 3/2018 | Witschi et al. |
| 10,272,078 B2 | 4/2019 | Witschi et al. |
| 2004/0254215 A1 | 12/2004 | Arend et al. |
| 2005/0090525 A1 | 4/2005 | Wiesner et al. |
| 2006/0018959 A1 | 1/2006 | Naganuma et al. |
| 2007/0155784 A1 | 7/2007 | Arend et al. |
| 2008/0234483 A1 | 9/2008 | Maejima et al. |
| 2008/0269301 A1 | 10/2008 | Yokoe et al. |
| 2009/0099203 A1* | 4/2009 | Blyth .................. A61K 9/2018 514/255.05 |
| 2010/0172984 A1* | 7/2010 | Padhi ..................... A61K 9/209 424/472 |
| 2012/0149712 A1* | 6/2012 | Klaus ..................... A61K 31/00 514/253.06 |
| 2015/0322015 A1 | 11/2015 | Witschi et al. |
| 2016/0120859 A1 | 5/2016 | Conca et al. |
| 2016/0194285 A1 | 7/2016 | Thompson et al. |
| 2016/0331741 A1 | 11/2016 | Witschi et al. |
| 2017/0035747 A1 | 2/2017 | Arend et al. |
| 2017/0190667 A1 | 7/2017 | Witschi et al. |
| 2019/0240213 A1 | 8/2019 | Arend et al. |

FOREIGN PATENT DOCUMENTS

| | | |
|---|---|---|
| JP | 2008044960 | 2/2008 |
| JP | 2010/248106 | 11/2010 |
| JP | 2010248106 | 11/2010 |
| JP | 2012/0176899 | 9/2012 |
| WO | WO-2003/053997 | 7/2003 |
| WO | WO-2004/052285 | 6/2004 |
| WO | WO-2004/108681 | 12/2004 |
| WO | WO-2007/065448 | 6/2007 |
| WO | WO-2007/097929 | 8/2007 |
| WO | WO-2007/115315 | 10/2007 |
| WO | WO-2009/073669 | 6/2009 |
| WO | WO-2009/100250 | 8/2009 |
| WO | WO-2010/022240 | 2/2010 |
| WO | WO-2010/056767 | 5/2010 |
| WO | WO-2010134556 | 11/2010 |
| WO | WO-2012/097331 | 7/2012 |
| WO | WO 2012/097331 A1 * | 7/2012 |
| WO | WO-2012/106472 | 8/2012 |
| WO | WO-2013/013609 | 1/2013 |
| WO | WO-2013/070908 | 5/2013 |
| WO | WO-2013/134660 | 9/2013 |
| WO | WO-2014/014834 | 1/2014 |
| WO | WO-2014/014835 | 1/2014 |
| WO | WO-2014/116849 | 7/2014 |
| WO | WO-2014/197660 | 12/2014 |

OTHER PUBLICATIONS

Ashizawa et al., Iyaku hin no takei genshou to shouseki no kagaku [Science of polymorphism and crystallization of medicament], Maruzen Planet Co., Ltd., Sep. 20, 2002, pp. 305-317.

Duro et al, Farmaco, Edizione Scientifica (1981), 36(6), pp. 400-411.

F. Podczeck, et al., "Geltain Alternatives and Additives," Pharmaeutical Capsules, Jan. 1, 2004, pp. 64-66.

Franklin et al., "Approaches to the design of anti-fibrotic drugs", Biochemical Society Transactions, 1991, pp. 812-815.

H. H. Tonnesen, "Photodecomposition of Drugs," Encyclopedia of Pharmaceutical Technology, Third Edition, 2007, pp. 2859-2865.

ICH Harmonised Tripartite Guideline, "Stability Testing: Photostability Testing of New Drug Substances and Porducts Q1B," Nov. 6, 1996, 11 pages. (Retrieved from the Internet: URL:http://www.ich.org/fileadmin/Public Web Site/ICH_Products/Guidelines/Quality/QIB/Step4/Q1B-Guideline.pdf [retrieved-on Jul. 9, 2013).

International Preliminary Report on Patentability for International Application No. PCT/US2004/017773 (WO/2004/108681) dated Dec. 8, 2005. (9 pages).

International Preliminary Report on Patentability for International Application No. PCT/US2013/050538 (WO/2014/014834) dated Jan. 20, 2015. (6 pages).

International Preliminary Report on Patentability for International Application No. PCT/US2013/050539 (WO/2014/014835) dated Jan. 20, 2015. (9 pages).

International Preliminary Report on Patentability for PCT/US2014/041021, dated Dec. 17, 2015.

International Search Report and Written Opinion for International Application No. PCT/US2013/050538 (WO/2014/014834) dated Sep. 17, 2013. (8 pages).

International Search Report and Written Opinion for International Application No. PCT/US2013/050539 (WO/2014/014835) dated Jul. 2, 2014. (13 pages).

International Search Report and Written Opinion for PCT/US2014/041021, dated Oct. 1, 2014.

Matsuoka, M., Kesshou takei no kiso to ouyou [Basic and application of crystal polymorphism], CMC Publishing Co., Ltd., Oct. 22, 2010, 1st edition of trade edition, pp. 105-117, and 181-191.

Written Opinion for International Application No. PCT/US2004/017773 (WO/2004/108681) dated Oct. 11, 2004. (8 pages).

Wu et al., Toxicology, 236, pp. 1-6, 2007.

* cited by examiner

PHARMACEUTICAL FORMULATIONS OF A HIF HYDROXYLASE INHIBITOR

CROSS REFERENCE TO RELATED APPLICATIONS

This application is a continuation of U.S. patent application Ser. No. 14/896,353, filed Dec. 4, 2015, now abandoned, which is a U.S. National Stage Application under 35 U.S.C. § 371 of International Application No. PCT/US2014/041021, filed Jun. 5, 2014, which claims the benefit under 35 U.S.C. § 119(e) of U.S. Provisional Application No. 61/831,909, filed Jun. 6, 2013, each of which is incorporated herein by reference in its entirety.

BACKGROUND

The present invention relates generally to pharmaceutical formulations of [(4-hydroxy-1-methyl-7-phenoxy-isoquinoline-3-carbonyl)-amino]-acetic acid.

[(4-Hydroxy-1-methyl-7-phenoxy-isoquinoline-3-carbonyl)-amino]-acetic acid (alternatively referred to herein as Compound A) is a potent inhibitor of hypoxia inducible factor (HIF) prolyl hydroxylase, as described in U.S. Pat. No. 7,323,475. HIF prolyl hydroxylase inhibitors are useful for increasing the stability and/or activity of HIF, and useful for, inter alia, treating and preventing disorders associated with HIF, including anemia, and ischemia- and hypoxia-related disorders.

It has recently been discovered that Compound A undergoes decomposition after exposure to light. Heretofore, pharmaceutical formulations of Compound A which provide the necessary photostability of the compound have not yet been taught.

SUMMARY

The present disclosure fulfills the need of providing photostability of Compound A and others by providing a pharmaceutical formulation comprising [(4-hydroxy-1-methyl-7-phenoxy-isoquinoline-3-carbonyl)-amino]-acetic acid, a pharmaceutically acceptable excipient and an effective amount of a photostabilizing agent. In one embodiment, the pharmaceutical formulation comprises less than about 0.2% w/w (based on the amount of active pharmaceutical ingredient ("API")) photodegradation product of [(4-hydroxy-1-methyl-7-phenoxy-isoquinoline-3-carbonyl)-amino]-acetic acid. In another embodiment, the photostabilizing agent blocks light at a wavelength range of between about 200 and about 550 nm.

In one embodiment, the photostabilizing agent comprises titanium dioxide and at least one additional dye. In one embodiment, the photostabilizing agent blocks light at a wavelength range of between about 200 and about 550 nm. In one embodiment, the dye is selected from the group consisting of a black dye, a blue dye, a green dye, a red dye, an orange dye, a yellow dye, and combinations thereof. In another embodiment, the dye is selected from the group consisting of a red dye, an orange dye, a yellow dye, and combinations thereof.

In one embodiment, the dye is selected from the group consisting of Allura Red AC, Allura Red AC aluminum lake, iron oxide red, iron oxide yellow, Sunset Yellow FCF, Sunset Yellow FCF aluminum lake, Indigotine, Indigotine aluminum lake, and combinations thereof.

In one embodiment, the pharmaceutical formulation comprises from about 20 mg to about 200 mg of [(4-hydroxy-1-methyl-7-phenoxy-isoquinoline-3-carbonyl)-amino]-acetic acid. In another embodiment, the pharmaceutical formulation comprises about 20 mg, about 50 mg, or about 100 mg of [(4-hydroxy-1-methyl-7-phenoxy-isoquinoline-3-carbonyl)-amino]-acetic acid.

In one embodiment, a solid dosage form comprises the pharmaceutical formulation and the solid dosage form is selected from a capsule, tablet, bead, granule, pellet, lozenge, pill, or gum. In another embodiment, the solid dosage form is a tablet. In another embodiment, the solid dosage form is a capsule.

The present disclosure provides a tablet comprising [(4-hydroxy-1-methyl-7-phenoxy-isoquinoline-3-carbonyl)-amino]-acetic acid, a pharmaceutically acceptable excipient and an effective amount of a photostabilizing agent. In one embodiment, the tablet comprises a tablet core and a coating. In some embodiments, the photostabilizing agent is blended into the tablet or the tablet core. In other embodiments, the tablet core comprises [(4-hydroxy-1-methyl-7-phenoxy-isoquinoline-3-carbonyl)-amino]-acetic acid and the pharmaceutically acceptable excipient, and the coating comprises the photostabilizing agent.

In one embodiment, the coating is present in the tablet in an amount that is from about 3% to about 8% w/w based on the weight of the tablet core. In another embodiment, the tablet core comprises from about 22% to about 28% w/w [(4-hydroxy-1-methyl-7-phenoxy-isoquinoline-3-carbonyl)-amino]-acetic acid (based on the weight of the tablet core). In yet another embodiment, the pharmaceutically acceptable excipient comprises lactose monohydrate, microcrystalline cellulose, povidone, croscarmellose sodium, and magnesium stearate.

In one embodiment, the coating comprises from about 0.1% to about 50% w/w photostabilizing agent (based on coating weight). In some embodiments, the photostabilizing agent comprises titanium dioxide and at least one additional dye selected from the group consisting of Allura Red AC, Allura Red AC aluminum lake, iron oxide red, iron oxide yellow, Sunset Yellow FCF, Sunset Yellow FCF aluminum lake, Indigotine, Indigotine aluminum lake, and combinations thereof. In another embodiment, the photostabilizing agent comprises titanium dioxide and Allura Red AC aluminum lake.

The present disclosure provides a capsule comprising [(4-hydroxy-1-methyl-7-phenoxy-isoquinoline-3-carbonyl)-amino]-acetic acid, a pharmaceutically acceptable excipient and an effective amount of a photostabilizing agent. In one embodiment, the capsule comprises a capsule fill and a capsule shell. In one embodiment, the capsule fill comprises [(4-hydroxy-1-methyl-7-phenoxy-isoquinoline-3-carbonyl)-amion]-acetic acid and the pharmaceutically acceptable excipient, and the capsule shell comprises the photostabilizing agent.

In one embodiment, the capsule fill comprises from about 12% to about 15% w/w [(4-hydroxy-1-methyl-7-phenoxy-isoquinoline-3-carbonyl)-amino]-acetic acid (based on the weight of the capsule fill). In another embodiment, the pharmaceutically acceptable excipient comprises lactose monohydrate, microcrystalline cellulose, povidone, croscarmellose sodium, and magnesium stearate.

In one embodiment, the capsule shell comprises the photostabilizing agent in an amount of from about 1.8% to about 6% w/w (based on the weight of the capsule shell). In some embodiments, the photostabilizing agent comprises titanium dioxide and at least one additional dye selected from the group consisting of Allura Red AC, iron oxide red, iron oxide yellow, and combinations thereof.

In a separate embodiment, a method of inhibiting the photodegradation of [(4-hydroxy-1-methyl-7-phenoxy-isoquinoline-3-carbonyl)-amino]-acetic acid is provided. The method comprises formulating [(4-hydroxy-1-methyl-7-phenoxy-isoquinoline-3-carbonyl)-amino]-acetic acid with an effective amount of a photostabilizing agent. In another embodiment, the photostabilizing agent comprises titanium dioxide and at least one additional dye.

In yet another embodiment, a method for treating, pretreating, or delaying onset or progression of a condition mediated at least in part by hypoxia inducible factor (HIF) is provided. The method comprises administering to a patient in need thereof, a pharmaceutical formulation, a tablet, or a capsule as described herein.

In still yet another embodiment, a method for treating, pretreating, or delaying onset or progression of anemia is provided. The method comprises administering to a patient in need thereof, a pharmaceutical formulation, a tablet, or a capsule as described herein.

DETAILED DESCRIPTION

Definitions

Figure 1:
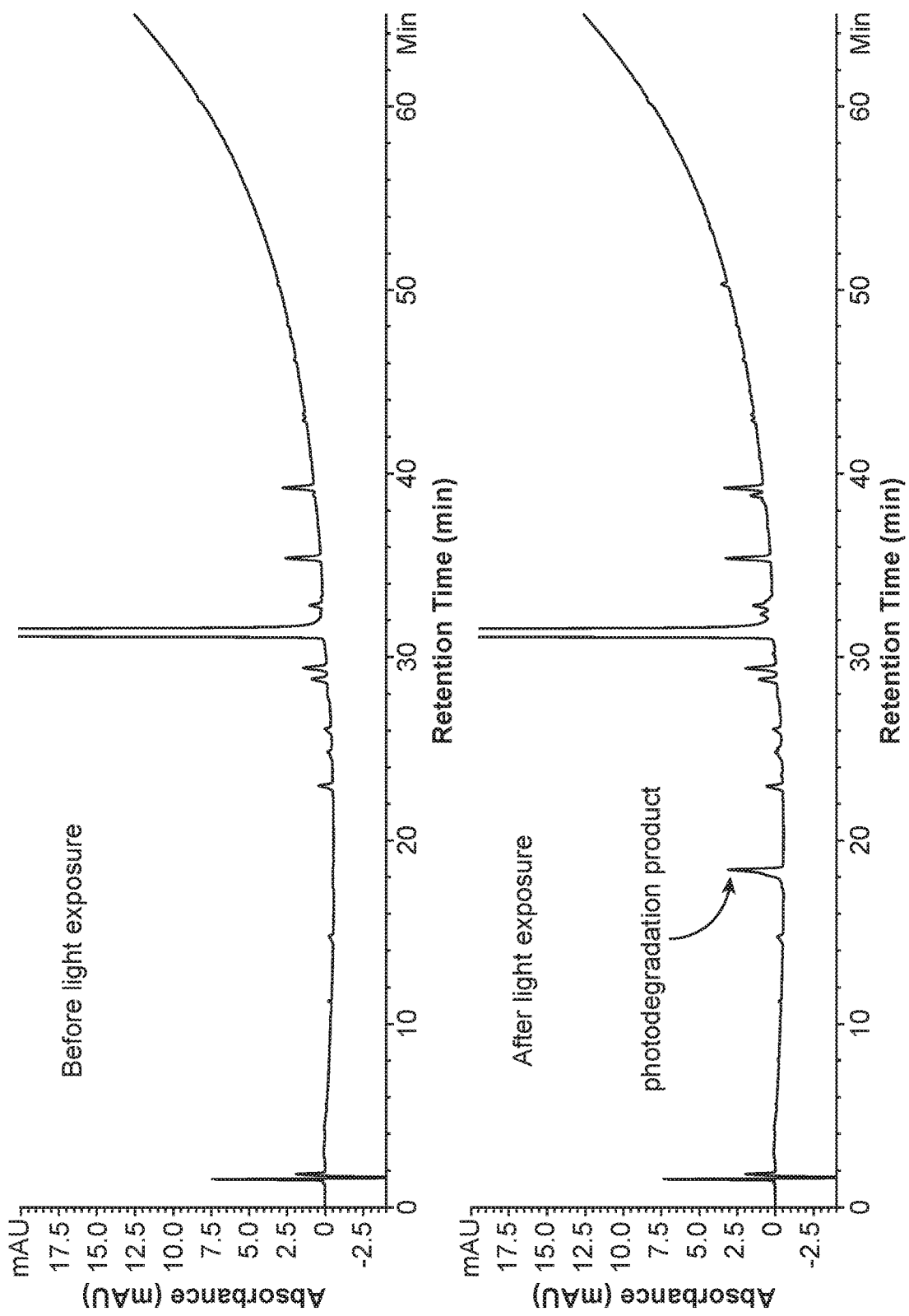
FIG. 1 illustrates the HPLC chromatograms of Compound A powders before and after exposure to sunlight. See Example 1 for details.

As used herein, the following terms have the following meanings.

The singular forms "a," "an," and "the" and the like include plural referents unless the context clearly dictates otherwise. Thus, for example, reference to "a compound" includes both a single compound and a plurality of different compounds.

The term "about" when used before a numerical designation, e.g., temperature, time, amount, and concentration, including a range, indicates approximations which may vary by ±10%, ±5% or ±1%.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmaceutical sciences, within the skill of the art. Such techniques are explained fully in the literature. (See, e.g., Gennaro, A. R., ed. (1990) Remington's Pharmaceutical Sciences, $18^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, $2^{11d}$ edition, Vols. I-III, Cold Spring Harbor Laboratory Press; Ausubel, F. M. et al., eds. (1999) Short Protocols in Molecular Biology, $4^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag; European Pharmacopoeia (Ph. Eur.), $7^{th}$ edition; The United States Pharmacopeia (USP) and the National Formulary (NF), USP 35-NF 30.

The term "API" is the abbreviation for "active pharmaceutical ingredient." As used herein, API refers to Compound A, or [(4-hydroxy-1-methyl-7-phenoxy-isoquinoline-3-carbonyl)-amino]-acetic acid.

The term "block light" refers to preventing or reducing the transmittance of light by absorbing, reflecting, refracting, diffracting, dispersing, and/or scattering light. When a dye blocks light at a certain wavelength range, the dye prevents or reduces the transmittance of light at that wavelength range by absorbing, reflecting, refracting, diffracting, dispersing, and/or scattering light.

The term "capsule" refers to a solid dosage form of a pharmaceutical formulation that comprises a capsule shell and a capsule fill.

The term "capsule fill" refers to the material enclosed within a capsule shell. Typically, the capsule fill comprises the active pharmaceutical ingredient (API) and one or more pharmaceutically acceptable excipients. The amount of API in the capsule fill can be expressed as a weight percent of API based on the total weight of the capsule fill (w/w %).

The term "capsule shell" refers to an outer layer of a capsule. The capsule shell comprises gelatin, cellulose polymers or other suitable materials which would allow for delivery of the API. The capsule shell may be a hard-shell consisting of a telescoping cap and body piece in a range of standard sizes. The cap and body piece may be sealed after addition of the capsule fill. Such hard-shelled capsules are typically used to deliver dry, powdered API in the capsule fill. The capsule shell may be a one-piece soft-shell used to deliver API as a solution or suspension in the capsule fill. In one embodiment, the capsule shell may comprise the photostabilizing agent. The amount of photostabilizing agent in the capsule shell can be expressed as a weight percent of photostabilizing agent based on the total weight of the capsule shell (% w/w). In one embodiment, the capsule shell comprises gelatin (a gelatin shell). In another embodiment, the capsule shell comprises hydroxypropylmethylcellulose (HPMC) (an HPMC shell).

The term "dye" as used throughout, includes true dyes (as defined in color and dye chemistry), dye lakes and pigments.

A true dye (as defined in color and dye chemistry) is a colored substance (including white color) that is soluble in water and/or an organic solvent and has an affinity to the substrate to which it is being applied such that color is imparted to the substrate. A dye lake is a solid, water insoluble form of a true dye. It is manufactured by mixing a true dye with an inert material such as aluminum hydroxide (aluminum lake, commonly used), barium sulfate, calcium sulfate, aluminum oxide (alumina). The amount of true dye in the lake is expressed as "dye strength." A pigment is a colored substance that is insoluble in water or organic solvent.

Dyes appear in colors because they absorb light in the visible spectrum (400-700 nm) and transmit, reflect or scatter light of other wavelengths in the visible spectrum. A "yellow dye" absorbs predominantly blue light and appears yellow in color. An "orange dye" absorbs predominantly green-blue light and appears orange in color. A "red dye" absorbs predominantly blue-green light and appears red in color. A "blue dye" absorbs predominantly yellow light and appears blue in color. A "green dye" predominantly absorbs red and orange light and appears green in color. A "black dye" absorbs light of the entire visible spectrum and appears black in color. Examples of red dye, yellow dye, green dye, blue dye and black dye are given in the following table. In addition to absorbing light, these dyes may block light through reflecting, refracting, diffracting, dispersing, and/or scattering light.

Different colors can also be obtained by mixing two or more dyes. For example, orange dyes of different shades can be obtained by mixing different amount of red and yellow dyes.

Dyes described in this application are referred to by their principal name. One of skill in the art would be able to readily ascertain the dye's US name or C.I. name (Color Index name). Non-limiting examples of dyes are listed in the following table.

| Color | Principal Name | US Name | C.I. Name |
|---|---|---|---|
| White dye | Titanium dioxide | | C.I. Pigment White 6 |
| Beige dye | Caramel | | C.I. Natural Brown 10 |
| Red dye | Allura Red or Allura Red AC | FD&C Red 40 | C.I. Food Red 17 |
| Red dye | Amaranth | | C.I. Food Red 9 |
| Red dye | Anthocyanin | | |
| Red dye | Azorubine | | C.I. Food Red 3 |
| Red dye | Beetroot Red | | |
| Red dye | Canthaxanthin | | C.I. Food Orange 8 |
| Red dye | Carmine | | C.I. Natural Red 4 |
| Red dye | D&C Red 33 | D&C Red 33 | C.I. Food Red 12 |
| Red dye | Eosine YS | D&C Red 22 | C.I. Food Red 87 |
| Red dye | Erythrosine | FD&C Red 3 (dye only) | C.I. Food Red 14 |
| Red dye | Iron oxide red or Red iron oxide | | C.I. Pigment Red 101 & 102 |
| Red dye | Lithol Rubine BK | D&C Red 7 | |
| Red dye | Phloxine B | D&C Red 28 | |
| Red dye | Ponceau 4R | | C.I. Food Red 7 |
| Red dye | Red 2G | | C.I. Food Red 10 |
| Yellow dye | Beta-Carotene | | C.I. Food Orange 5 |
| Yellow dye | Mixed Carotenes | | C.I. Food Orange 5 |
| Yellow dye | Curcumin | | C.I. Natural Yellow 3 |
| Yellow dye | D&C Yellow 10 | D&C Yellow 10 | C.I. Food Yellow 13 |
| Yellow dye | Iron oxide yellow or Yellow iron oxide | | C.I. Pigment Yellow 42&43 |
| Yellow dye | Quinoline Yellow WS | | C.I. Food Yellow 13 |
| Yellow dye | Riboflavin | | |
| Yellow dye | Sunset Yellow FCF | FD&C Yellow 6 | C.I. Food Yellow 3 |
| Yellow dye | Tartrazine | FD&C Yellow 5 | C.I. Food Yellow 4 |
| Green dye | Chlorophylls and Chlorophyllins | | C.I. Natural Green 3 |
| Green dye | Cu Complexes of Chlorophylls and Chlorophyllins | | C.I. Natural Green 3 |
| Green dye | Fast Green FCF | FD&C Green 3 | C.I. Food Green 3 |
| Green dye | Green S | | C.I. Food Green 4 |
| Blue dye | Brilliant Blue FCF | FD&C Blue 1 | C.I. Food Blue 2 |
| Blue dye | Indigotine | FD&C Blue 2 | C.I. Food Blue 1 |
| Blue dye | Patent Blue V | | C.I. Food Blue 5 |
| Black dye | Brilliant Black BN | | C.I. Food Black 1 |
| Black dye | Iron oxide black (or Black iron oxide) | | C.I. Pigment Black 11 |
| Black dye | Vegetable Carbon | | C.I. Food Black 3 |

The term "pharmaceutically acceptable" indicates that the material does not have properties that would cause one of skill in the art to avoid administration of the material to a patient, taking into consideration the disease or conditions to be treated and the respective route of administration. Further, the material is considered to be safe for administration in humans or animals.

The term "excipient" or "pharmaceutically acceptable excipient" refers to pharmacologically inactive substances that are added to a pharmaceutical preparation in addition to the active pharmaceutical ingredient. Excipients may take the function of vehicle, diluent, release, disintegration or dissolution modifying agent, absorption enhancer, stabilizer or a manufacturing aid among others. Excipients may include fillers (diluents), binders, disintegrating agents, lubricants, and glidants. Examples of excipient classes frequently used are listed below.

"Diluent or filler" refers to substances that are used to dilute the active pharmaceutical ingredient prior to delivery. Diluents can also serve as stabilizers. Non-limiting examples of diluents include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

"Binder" refers to any pharmaceutically acceptable substance which can be used to bind the active and inert components together to maintain cohesive and discrete portions. Non-limiting examples of binders include hydroxypropylcellulose, hydroxypropylmethylcellulose, povidone, and ethyl cellulose.

"Disintegrant or disintegrating agents" refers to a substance which, upon addition to a solid preparation, facilitates its break-up or disintegration after administration and permits the release of an active ingredient as efficiently as possible to allow for its rapid dissolution. Non-limiting examples of disintegrants include maize starch, sodium starch glycolate, croscarmellose sodium, crospovidone, microcrystalline cellulose, modified corn starch, sodium carboxymethyl starch, povidone, pregelatinized starch, and alginic acid.

"Lubricant" refers to an excipient which is added to a powder blend to prevent the compacted powder mass from sticking to the equipment during the tableting or encapsulation process. It aids the ejection of the tablet form the dies, and can improve powder flow. Non-limiting examples of lubricants include magnesium stearate, stearic acid, silica, fats, calcium stearate, polyethylene glycol, sodium stearyl fumarate, talc, or fatty acids including lauric acid, oleic acid, and $C_8/C_{10}$ fatty acid.

"Glidant" as used herein is intended to mean agents used in tablet and capsule formulations to improve flow-properties during tablet compression and to produce an anti-caking effect. Non-limiting examples of glidants include colloidal silicon dioxide, talc, fumed silica, starch, starch derivatives, and bentonite.

The term "formulate" or "formulating" refers to combining the active pharmaceutical ingredient with one or more other components, for example, including without limitation one or more pharmaceutically acceptable excipients, stabilizing agents, photostabilizing agents, coatings, capsule shells, etc., in a process, which produces a final medicinal product. Examples of medicinal product include, but not limited to, tablets, pills, dragees, capsules, gels, syrups, slurries, suspensions, aerosol sprays, and solutions for injection.

The term "gelatin" refers to a solid substance derived from collagen and can be obtained from various animal by-productions. It is commonly used as a gelling agent in pharmaceuticals.

The term "light exposure", refers any light exposure, including sunlight (or natural light), indoor light and exposure to light under International Conference of Harmonization (ICH) conditions. "ICH light exposure" means exposure to light under ICH conditions, which may be ICH Option 1 or ICH Option 2. Under ICH conditions, the samples are exposed to light providing an overall illumination of not less than 1.2 million lux hours and an integrated near ultraviolet energy of not less than 200 watt hours/square meter, using one of the two options described below as light sources (ICH Q1B).

a. ICH Option 1:

Any light source that is designed to produce an output similar to the D65/ID65 emission standard such as an artificial daylight fluorescent lamp combining visible and ultraviolet (UV) outputs, xenon, or metal halide lamp. D65 is the internationally recognized standard for outdoor daylight as defined in ISO 10977 (1993). ID65 is the equivalent indoor indirect daylight standard. For a light source emitting significant radiation below 320 nanometers (nm), an appropriate filter(s) may be fitted to eliminate such radiation.

b. ICH Option 2:

A cool white fluorescent lamp designed to produce an output similar to that specified in ISO 10977 (1993); and A near UV fluorescent lamp having a spectral distribution from 320 nm to 400 nm with a maximum energy emission between 350 nm and 370 nm; a significant proportion of UV should be in both bands of 320 to 360 nm and 360 to 400 nm.

The term "photostabilizing agent" is an agent that prevents or reduces the photodegradation or photodecomposition of a molecule upon exposure to light (light under ICH condition, sunlight, indoor light, etc.). In other words, the photostabilizing agent functions to prevent or reduce the formation of photodegradation products. Typically, the photostabilizing agent prevents or reduces the photodegradation of the light-sensitive molecule by blocking the exposure of the molecule to light within a wavelength range. Non-limiting examples of photostabilizing agents include pigments, dyes, dye lakes, and the like.

The term "photodegradation" and "photodecomposition" are used interchangeably throughout the disclosure.

The term "effective amount" of a photostabilizing agent refers to the amount of a photostabilizing agent in a pharmaceutical formulation that is sufficient to prevent or reduce the photodegradation of the active pharmaceutical ingredients (API), such that the amount of photodegradation product(s) that is produced is limited to a desired maximum level under specified light conditions. In the embodiments described herein, the effective amount of a photostabilizing agent is the amount sufficient to limit the amount of photodegradation product of Compound A that is produced to a level that is less than about 0.2% w/w Compound A (or 2000 ppm), under ICH conditions. In some embodiments, the effective amount of photostabilizing agent may limit the amount of photodegradation product of Compound A that is produced to a level that is less than about 0.15% w/w Compound A, less than about 0.1% w/w Compound A, or less than 0.05% w/w Compound A. As will be apparent to one skilled in the formulations art, the effective amount of a stabilizing agent will vary with the particular agent used. Using the disclosure herein, particularly the analytical methods described in the examples, and the general knowledge in the formulations art, one of ordinary skill in the art can readily determine the amount of any particular agent (or combination of agents) that will achieve the level of photoprotection (i.e., reduction of the production of photodegradation product) sufficient to limit photodegradation product to the desired maximum level.

The term "photodegradation product" as used herein refers to a new molecule that is formed from Compound A upon exposing Compound A to light. The photodegradation product may be detected by a variety of standard analytical methods (e.g., high-performance liquid chromatography (HPLC), liquid chromatography-mass spectrometry (LC-MS), gas chromatography (GC), nuclear magnetic resonance (NMR), Fourier transform infrared spectroscopy (FTIR), etc.). In one embodiment, the photodegradation product may be detected and measured by HPLC, as further described in Example 1.

The term "tablet" refers to a solid dosage form of a pharmaceutical formulation in which the API is blended with one or more pharmaceutically acceptable excipient and compressed into a single solid final dosage form. Tablets can be produced in a wide variety of sizes, shapes, and surface markings. Tablets may be uncoated or coated by a variety of techniques that are well known in the art. Typically, a tablet comprises a tablet core and a coating.

The term "tablet core" refers to the inner part of a tablet containing the API and one or more pharmaceutically acceptable excipient compressed into the desired shape but not including the coating. The amount of API in the tablet core can be expressed as a percent of API by weight based on the total weight of the tablet core, % w/w.

The term "coating" refers to an outer part of a tablet. For tablets as described herein, the coating is applied to the outer surface of the tablet core and typically adheres thereto. The coating may provide one or more of the following properties: taste masking, protecting the API(s) from photodegradation, ease of administration, release modification of the API(s), dust protection, or unique appearance (colors), among other things. Non-limiting examples of coating materials include polyvinylalcohol-based compounds, hydroxyethylcellulose, hydroxypropylmethylcellulose, carboxymethylcellulose sodium, polyethylene glycol 4000 and cellulose acetate phthalate. In one embodiment, the coating is a polyvinylalcohol-based coating. The amount of coating that is applied over the outer surface of tablet core can be expressed as a percent of coating by weight based on the weight of the tablet core, % w/w. In one embodiment, the coating may comprise a photostabilizing agent such as a dye. The amount of dye within a coating can be expressed as a percent of dye weight based on the weight of the coating % w/w. Alternatively, the amount of dye within a coating can be expressed as the amount of the dye applied per surface area unit of the tablet core, mg/cm$^2$.

The term "anemia" as used herein refers to any abnormality in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels. Anemia can arise due to conditions such as acute or chronic kidney disease, infections, inflammation, cancer, irradiation, toxins, diabetes, and surgery. Infections may be due to, e.g., virus, bacteria, and/or parasites, etc. Inflammation may be due to infection, autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia is further associated with radiation therapy, chemotherapy, and kidney dialysis. Anemia is also associated with HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure that result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively herein and refer to any condition deviating from normal.

"Treatment", "treating", and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition.

"Administration" refers to introducing an agent into a patient. A therapeutic amount can be administered, which can be determined by the treating physician or the like. An oral route of administration is preferred for Compound A. The related terms and phrases "administering" and "administration of", when used in connection with a compound or pharmaceutical formulation (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In any event, administration entails delivery of the drug to the patient.

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J Biol. Chem.* 275:25733-25741; and Tanimoto et al. (2000) *EMBO J.* 19:4298-4309.)

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include anemic conditions and tissue damage or disorders associated with ischemic or hypoxic conditions.

The terms "HIF prolyl hydroxylase", "PHD", "EGLN", and "HIF PH" refer to any enzyme that modifies the alpha subunit of HIF protein by hydroxylation of one or more proline residues. HIF PH includes members of the Egl-Nine (EGLN) gene family described by Taylor (2001, *Gene* 275:125-132), and characterized by Aravind and Koonin (2001, *Genome Biol* 2: RESEARCH 0007), Epstein et al. (2001, *Cell* 107:43-54), and Bruick and McKnight (2001, *Science* 294:1337-1340). HIF PH2, as used in exemplary assays described herein (infra), may be any HIF PH2, also referred to as PHD2, e.g., human EGLN1 (GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to HIF PH1, also referred to as PHD1, e.g., human EGLN2 isoform 1 (GenBank Accession No. CAC42510; Taylor, supra), human EGLN2 isoform 3 (GenBank Accession No. NP 542770), mouse EGLN2 (GenBank Accession No. CAC42516), and rat EGLN2 (GenBank Accession No. AA046039), etc.; and any HIF PH3, also referred to as PDH3, e.g. human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present disclosure, EGLN may include *Caenorhabditis elegans* EGL-9 (GenBank Accession No. AAD56365) and *Drosophila melanogaster* CG1114 gene product (GenBank Accession No. AAF52050).

Pharmaceutical Formulations

The compound [(4-hydroxy-1-methyl-7-phenoxy-isoquinoline-3-carbonyl)-amino]-acetic acid (Compound A) is a potent inhibitor of hypoxia inducible factor (HIF) prolyl hydroxylase and has the following formula:

Compound A

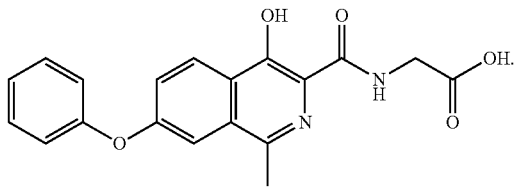

As described in the examples herein, it has recently been discovered that Compound A undergoes photodecomposition after light exposure to convert to a photodegradation product. The present invention provides compositions (formulations) and methods that prevent or reduce the amount of photodegradation of Compound A and limit the amount of photodegradation product.

The pharmaceutical formulations described herein protect Compound A from photodegradation. Accordingly, in one embodiment the invention provides a pharmaceutical formulation comprising [(4-hydroxy-1-methyl-7-phenoxy-isoquinoline-3-carbonyl)-amino]-acetic acid, a pharmaceutically acceptable excipient, and an effective amount of a photostabilizing agent. In a further embodiment, the invention provides a pharmaceutical formulation comprising [(4-hydroxy-1-methyl-7-phenoxy-isoquinoline-3-carbonyl)-amino]-acetic acid, a pharmaceutically acceptable excipient, and an effective amount of a photostabilizing agent, wherein the pharmaceutical formulation comprises less than about 0.2% w/w (based on the amount of API, [(4-hydroxy-1-methyl-7-phenoxy-isoquinoline-3-carbonyl)-amino]-acetic acid) photodegradation product of [(4-hydroxy-1-methyl-7-phenoxy-isoquinoline-3-carbonyl)-amino]-acetic acid.

In one embodiment, the pharmaceutical formulation comprises less than about 0.2% w/w (equivalent to 2000 ppm, based on the amount of API) photodegradation product of [(4-hydroxy-1-methyl-7-phenoxy-isoquinoline-3-carbonyl)-amino]-acetic acid after exposure of the formulation to light under ICH conditions. The amount of photodegradation product can be readily determined by one of ordinary skill in the art based on the disclosure herein using routine analytical methods. If multiple determinations of the amount of photodegradation product are made, the mean value of the amount of photodegradation product from multiple determinations is no more than about 0.2% w/w. The condition of the light exposure (the kind of light source, the power of the light source and the duration of light exposure) is the ICH condition defined herein. The amount of photodegradation product that is produced is readily determined by the methods described herein, particularly by HPLC method. One skilled in the formulations art can readily determine the effective amount of photostabilizing agent sufficient to limit the amount of the photodegradation product, based on the guidance and examples provided herein.

In one embodiment, the photostabilizing agent is selected to prevent or reduce photodegradation of Compound A. In one embodiment, the photostabilizing agent prevents or reduces photodegradation through effectively blocking light. In one embodiment, the photostabilizing agent prevents or reduces photodegradation through effectively blocking light in the wavelength range of about 100 to about 800 nm, about 150 to about 700 nm, about 200 to about 550 nm, or about 360 to about 440 nm. In one embodiment, the present invention provides a pharmaceutical formulation comprising [(4-hydroxy-1-methyl-7-phenoxy-isoquinoline-3-carbonyl)-amino]-acetic acid, a pharmaceutically acceptable excipient, and an effective amount of a photostabilizing agent, wherein the photostabilizing agent comprises titanium dioxide and at least one additional dye. In one embodiment, the dye blocks light at a wavelength range of about 100 to about 800 nm, about 150 to about 700 nm, about 200 to about 550 nm, or about 360 to about 440 nm.

In some embodiments, the photostabilizing agent comprises a soluble dye, a dye lake, a pigment or a combination thereof. In one embodiment, the photostabilizing agent comprises titanium dioxide and at least one additional dye. In one embodiment, the dye is selected from the group consisting of a black dye, a blue dye, a green dye, a red dye, an orange dye, a purple dye, a violet dye, a yellow dye, and combinations thereof. In another embodiment, the dye is selected from the group consisting of a black dye, a blue dye, a green dye, a red dye, an orange dye, a yellow dye, and combinations thereof. In yet another embodiment, the dye is selected from the group consisting of a red dye, an orange dye, a yellow dye, and combinations thereof.

In another embodiment, the additional dye is selected from the group consisting of Caramel, iron oxide black, iron oxide red, iron oxide yellow, Allura Red AC, Allura Red AC aluminum lake, Carmine, Erythrosine, beta-carotene or mixtures of carotenes, Curcumin, Sunset Yellow FCF, Sunset Yellow FCF aluminum lake, Tartrazine, chlorophylls and chlorophyllins or Cu complexes thereof, Fast Green FCF, Brilliant Blue FCF, Indigotine, Indigotine aluminum lake, and combinations thereof.

In one embodiment, the additional dye is selected from the group consisting of iron oxide black, iron oxide red, iron oxide yellow, Allura Red AC, Allura Red AC aluminum lake, Carmine, Erythrosine, beta-carotene or mixtures of carotenes, Sunset Yellow FCF, Sunset Yellow FCF aluminum lake, chlorophylls and chlorophyllins or Cu complexes thereof, Fast Green FCF, Indigotine, Indigotine aluminum lake, and combinations thereof.

In one embodiment, the additional dye is selected from the group consisting of iron oxide black, iron oxide red, iron oxide yellow, Allura Red AC, Allura Red AC aluminum lake, Carmine, beta-carotene or mixtures of carotenes, Sunset Yellow FCF, Sunset Yellow FCF aluminum lake, Indigotine, Indigotine aluminum lake, and combinations thereof.

In another embodiment, the additional dye is selected from the group consisting of Allura Red AC, Allura Red AC aluminum lake, iron oxide red, iron oxide yellow, Sunset Yellow FCF, Sunset Yellow FCF aluminum lake, Indigotine, Indigotine aluminum lake, and combinations thereof.

In one embodiment, the photostabilizing agent comprises titanium dioxide and Allura Red AC aluminum lake. In one embodiment, the photostabilizing agent comprises iron oxide red and titanium dioxide. In one embodiment, the photostabilizing agent comprises Allura Red AC, iron oxide yellow, and titanium dioxide. In one embodiment, the photostabilizing agent comprises iron oxide red, Allura Red AC, iron oxide yellow, and titanium dioxide. In one embodiment, the photostabilizing agent comprises iron oxide red, iron oxide yellow, and titanium dioxide. In one embodiment, the photostabilizing agent comprises iron oxide yellow and titanium dioxide.

In some embodiments, the photostabilizing agent comprises titanium dioxide. In some embodiment, the photostabilizing agent comprises a dye selected from the group consisting of a black dye, a blue dye, a green dye, a red dye, an orange dye, a purple dye, a violet dye, a yellow dye, and combinations thereof. In another embodiment, the photostabilizing agent comprises a dye selected from the group consisting of a black dye, a blue dye, a green dye, a red dye, an orange dye, a yellow dye, and combinations thereof. In yet another embodiment, the photostabilizing agent comprises a dye selected from the group consisting of a red dye, an orange dye, a yellow dye, and combinations thereof.

In one embodiment, the photostabilizing agent comprises a dye selected from the group consisting of Caramel, iron oxide black, iron oxide red, iron oxide yellow, Allura Red AC, Allura Red AC aluminum lake, Carmine, Erythrosine, beta-carotene or mixtures of carotenes, Curcumin, Sunset Yellow FCF, Sunset Yellow FCF aluminum lake, Tartrazine, chlorophylls and chlorophyllins or Cu complexes thereof, Fast Green FCF, Brilliant Blue FCF, Indigotine, Indigotine aluminum lake, and combinations thereof.

In one embodiment, the pharmaceutical formulation comprises from about 1 mg to about 400 mg of [(4-hydroxy-1-methyl-7-phenoxy-isoquinoline-3-carbonyl)-amino]-acetic acid. In another embodiment, the pharmaceutical formulation comprises from about 20 mg to about 200 mg of [(4-hydroxy-1-methyl-7-phenoxy-isoquinoline-3-carbonyl)-amino]-acetic acid. In another embodiment, the pharmaceutical formulation comprises about 1 mg, about 5 mg, about 10 mg, about 15 mg, about 20 mg, about 25 mg, about 50 mg, about 75 mg, about 100 mg, about 125 mg, about 150 mg, about 175 mg, about 200 mg, about 250 mg, about 300 mg, about 350 mg, or about 400 mg of [(4-hydroxy-1-methyl-7-phenoxy-isoquinoline-3-carbonyl)-amino]-acetic acid. In yet another embodiment, the pharmaceutical formulation comprises about 20 mg, about 50 mg, or about 100 mg of [(4-hydroxy-1-methyl-7-phenoxy-isoquinoline-3-carbonyl)-amino]-acetic acid. In yet another embodiment, the pharmaceutical formulation comprises about 20 mg, or about 50 mg of [(4-hydroxy-1-methyl-7-phenoxy-isoquinoline-3-carbonyl)-amino]-acetic acid.

In one embodiment, the pharmaceutical formulation comprises from about 1% to about 90% w/w [(4-hydroxy-1-methyl-7-phenoxy-isoquinoline-3-carbonyl)-amino]-acetic acid. In another embodiment, the pharmaceutical formulation comprises from about 0.1% to about 50% w/w photostabilizing agent. In another embodiment, the pharmaceutical formulation comprises from about 1% to about 7% w/w photostabilizing agent. In each embodiment, the pharmaceutical formulation comprises a pharmaceutically acceptable excipient. The pharmaceutically acceptable excipient may include fillers such as sugars, including lactose, lactose monohydrate, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, carboxymethylcellulose sodium, microcrystalline cellulose and/or polyvinylpyrrolidone (PVP or povidone), disintegrating agents, such as the cross-linked polyvinyl pyrrolidone, agar, croscarmellose sodium or alginic acid or a salt thereof such as sodium alginate, and wetting agents such as sodium dodecyl sulfate or lubricants such as magnesium stearate. In one embodiment, the pharmaceutical formulation comprises one or more pharmaceutically acceptable excipients selected from lactose monohydrate, microcrystalline cellulose, povidone, croscarmellose sodium, or magnesium stearate.

In one embodiment, a solid dosage form comprises the pharmaceutical formulation and the solid dosage form is selected from a capsule, tablet, bead, granule, pellet, lozenge, pill, or gum. In another embodiment, the solid dosage form is a tablet. In another embodiment, the solid dosage form is a capsule.

Tablet

The present disclosure provides a tablet comprising [(4-hydroxy-1-methyl-7-phenoxy-isoquinoline-3-carbonyl)-amino]-acetic acid, a pharmaceutically acceptable excipient and an effective amount of a photostabilizing agent. In one embodiment, the tablet comprises a tablet core and a coating.

In some embodiments, the photostabilizing agent is blended into the tablet or the tablet core. A tablet or a tablet core is prepared by mixing API with one or more excipients such as fillers (diluents), binders, disintegrating agents, lubricants, and glidants; and then by compressing the mixture. In the embodiments in which the photostabilizing agent is blended into the tablet or the tablet core, the photostabilizing agent is mixed (blended) with API and excipient, and then the mixture is compressed to form a tablet or a tablet core. Methods of preparing such compressed tablets and tablet cores are well known in the pharmaceutical arts.

In one embodiment, the tablet comprises a tablet core and a coating, wherein the tablet core comprises [(4-hydroxy-1-methyl-7-phenoxy-isoquinoline-3-carbonyl)-amino]-acetic acid and the pharmaceutically acceptable excipient, and the coating comprises the photostabilizing agent.

Based on the description and examples provided herein and routine practices in the formulations art, one of skill in the art will be able to determine the appropriate amount of coating containing the photostabilizing agent in terms of density and thickness to provide the photostabilization. In one embodiment, the coating is present in the tablet in an amount that is about 3% to about 8% w/w based on the weight of the tablet core. For example, from about 7% to about 8% w/w of coating can be applied to a 80 mg tablet core; from about 5% to about 6% w/w of coating can be applied to a 200 mg tablet core; or from about 4% to about 5% w/w of coating can be applied to a 400 mg tablet core. The amount of the photostabilizing agent in these coatings may vary and is described herein (for example, see Example 2). Non-limiting examples of coating include polyvinylalcohol-based, hydroxyethylcellulose, hydroxypropylmethylcellulose, carboxymethylcellulose sodium, polyethylene glycol 4000 and cellulose acetate phthalate coatings. In one embodiment, the coating is a polyvinylalcohol-based coating.

In one embodiment, the photostabilizing agent in the tablet comprises titanium dioxide and at least one additional dye selected from the group consisting of Allura Red AC, Allura Red AC aluminum lake, iron oxide red, iron oxide yellow, Sunset Yellow FCF, Sunset Yellow FCF aluminum lake, Indigotine, Indigotine aluminum lake, and combinations thereof. In another embodiment, the photostabilizing agent comprises titanium dioxide and Allura Red AC aluminum lake.

One of skill in the art will be able to determine the effective amount of photostabilizing agent needed to prevent or reduce the photodegradation. The amount of photostabilizing agent in the coating can be described as % w/w, percent weight of the photostabilizing agent based on the coating weight. In one embodiment, the coating comprises from about 0.1% to about 50% w/w photostabilizing agent (based on coating weight). In another embodiment, the coating comprises from about 0.5% to about 40% w/w photostabilizing agent (based on coating weight). In another embodiment, the coating comprises from about 2% to about 35% photostabilizing agent (based on coating weight).

The amount of photostabilizing agent in the coating can also be described as the weight of the photostabilizing agent applied per surface area unit of the tablet core (mg/cm$^2$). To determine the amount of photostabilizing agent needed to prevent or reduce photodegradation, the tablet core can be coated with various amounts of coatings and each coating may contain different dyes at different quantities. Photodegradation can be monitored by the appearance of photodegradation product, if any, upon light exposure (either under ICH condition or sunlight). Example 2 describes various coatings with different dye compositions and their photostabilization results. In the coating, when dye is present in the form of its aluminum lake, the amount of dye refers to the total amount of pure dye in its aluminum lake, not including other components of the aluminum lake.

In one embodiment, the photostabilizing agent in the coating comprises at least about 0.1 mg/cm$^2$ titanium dioxide and at least one additional dye selected from the group consisting of:
  at least about 0.1 mg/cm$^2$ Allura Red AC;
  at least about 0.1 mg/cm$^2$ Allura Red AC in aluminum lake;
  at least about 0.004 mg/cm$^2$ iron oxide red;
  at least about 0.009 mg/cm$^2$ iron oxide yellow;
  at least about 0.01 mg/cm$^2$ Sunset Yellow FCF; and
  at least about 0.01 mg/cm$^2$ Sunset Yellow FCF in aluminum lake;
  wherein the amount of photostabilizing agent is based on the surface area of the tablet core.

In another embodiment, the photostabilizing agent in the coating comprises from about 0.1 to about 2 mg/cm$^2$ titanium dioxide and at least one additional dye selected from the group consisting of:
  from about 0.1 to about 0.4 mg/cm$^2$ Allura Red AC;
  from about 0.1 to about 0.4 mg/cm$^2$ Allura Red AC in aluminum lake;
  from about 0.004 to about 0.4 mg/cm$^2$ iron oxide red;
  from about 0.009 to about 0.2 mg/cm$^2$ iron oxide yellow;
  from about 0.01 to 0.03 mg/cm$^2$ Sunset Yellow FCF, and
  from about 0.01 to 0.03 mg/cm$^2$ Sunset Yellow FCF in aluminum lake;
  wherein the amount of photostabilizing agent is based on the surface area of the tablet core.

In yet another embodiment, the photostabilizing agent in the coating comprises, based on surface area of the tablet core, from about 0.1 to about 2 mg/cm$^2$ or from about 0.1 to about 0.4 mg/cm$^2$ titanium dioxide, and from about 0.1 to about 0.4 mg/cm$^2$ Allura Red AC or Allura Red AC in aluminum lake.

Further examples of various suitable amounts of photostabilizing agents applied to tablet cores are given in Example 2.

In some embodiments, the tablet core comprises from about 1% to about 90% w/w, from about 5% to about 80% w/w, from about 5% to about 40% w/w, from about 11% to about 30% w/w, 20% to about 30% w/w or from about 22% to about 28% w/w [(4-hydroxy-1-methyl-7-phenoxy-isoquinoline-3-carbonyl)-amino]-acetic acid, and a pharmaceutically acceptable excipient.

In some embodiments, the tablet core comprises about 1 mg to about 400 mg, or about 20 mg to about 200 mg of [(4-hydroxy-1-methyl-7-phenoxy-isoquinoline-3-carbonyl)-amino]-acetic acid, and a pharmaceutically acceptable excipient. In other embodiments, the tablet core comprises about 1 mg, about 5 mg, about 10 mg, about 15 mg, about 20 mg, about 25 mg, about 50 mg, about 75 mg, about 100 mg, about 125 mg, about 150 mg, about 175 mg, about 200 mg, about 250 mg, about 300 mg, about 350 mg, or about 400 mg of [(4-hydroxy-1-methyl-7-phenoxy-isoquinoline-3-carbonyl)-amino]-acetic acid, and a pharmaceutically acceptable excipient. In other embodiments, the tablet core comprises about 20 mg, about 50 mg, or about 100 mg of [(4-hydroxy-1-methyl-7-phenoxy-isoquinoline-3-carbonyl)-amino]-acetic acid, and a pharmaceutically acceptable excipient.

Suitable excipients are, for example, fillers such as sugars, including lactose, lactose monohydrate, sucrose, mannitol, or sorbitol; cellulose preparations such as, for example, maize starch, wheat starch, rice starch, potato starch, gelatin, gum tragacanth, methyl cellulose, hydroxypropylmethylcellulose, carboxymethylcellulose sodium, microcrystalline cellulose and/or polyvinylpyrrolidone (PVP or povidone). If desired, disintegrating agents may be added, such as the cross-linked polyvinyl pyrrolidone, agar, croscarmellose sodium or alginic acid or a salt thereof such as sodium alginate. Also, wetting agents such as sodium dodecyl sulfate or lubricants such as magnesium stearate may be included.

In one embodiment, the pharmaceutically acceptable excipient comprises lactose monohydrate, microcrystalline cellulose, povidone, croscarmellose sodium, and magnesium stearate.

The present disclosure provides a tablet comprising a tablet core and a coating, wherein the tablet core comprises [(4-hydroxy-1-methyl-7-phenoxy-isoquinoline-3-carbonyl)-amino]-acetic acid and a pharmaceutically acceptable excipient, and the coating comprises an effective amount of a photostabilizing agent, wherein the coating is present in an amount from about 3% to about 8% w/w (based on the weight of the tablet core).

In one embodiment, the tablet core comprises from about 22% to about 28% w/w [(4-hydroxy-1-methyl-7-phenoxy-isoquinoline-3-carbonyl)-amino]-acetic acid (based on the weight of the tablet core) and a pharmaceutically acceptable excipient. In one embodiment, the pharmaceutically acceptable excipient comprises lactose monohydrate, microcrystalline cellulose, povidone, croscarmellose sodium, and magnesium stearate. In another embodiment, the tablet core comprises from about 20 mg to about 200 mg [(4-hydroxy-1-methyl-7-phenoxy-isoquinoline-3-carbonyl)-amino]-acetic acid. In another embodiment, the tablet core comprises about 20 mg, about 50 mg or about 100 mg [(4-hydroxy-1-methyl-7-phenoxy-isoquinoline-3-carbonyl)-amino]-acetic acid.

In one embodiment, the photostabilizing agent comprises titanium dioxide and at least one additional dye selected from the group consisting of Allura Red AC, Allura Red AC aluminum lake, iron oxide red, iron oxide yellow, Sunset Yellow FCF, Sunset Yellow FCF aluminum lake, Indigotine, Indigotine aluminum lake, and combinations thereof. In another embodiment, the photostabilizing agent comprises titanium dioxide and Allura Red AC aluminum lake. In yet another embodiment, the coating comprises from about 0.1 to about 0.4 mg/cm$^2$ titanium dioxide and from about 0.1 to about 0.4 mg/cm$^2$ Allura Red AC in aluminum lake wherein the amount of titanium dioxide and Allura Red AC in aluminum lake is based on surface area of the tablet core.

The present disclosure provides a tablet comprising a tablet core and a coating, wherein the tablet core comprises [(4-hydroxy-1-methyl-7-phenoxy-isoquinoline-3-carbonyl)-amino]-acetic acid and a pharmaceutically acceptable excipient, and the coating comprises an effective amount of a photostabilizing agent, wherein the coating is present in an amount from about 3% to about 8% w/w (based on the weight of the tablet core), wherein the tablet core comprises about 20 mg, about 50 mg or about 100 mg of [(4-hydroxy-1-methyl-7-phenoxy-isoquinoline-3-carbonyl)-amino]-acetic acid, lactose monohydrate, microcrystalline cellulose, povidone, croscarmellose sodium, and magnesium stearate; and wherein the photostabilizing agent comprises 0.1 to about 0.4 mg/cm$^2$ titanium dioxide and from about 0.1 to about 0.4 mg/cm$^2$ Allura Red AC in aluminum lake wherein the amount of titanium dioxide and Allura Red AC in aluminum lake is based on surface area of the tablet core.

Capsule

The present disclosure provides a capsule comprising [(4-hydroxy-1-methyl-7-phenoxy-isoquinoline-3-carbonyl)-amino]-acetic acid, a pharmaceutically acceptable excipient and an effective amount of a photostabilizing agent. In one embodiment, the capsule comprises a capsule fill and a capsule shell, wherein the capsule fill comprises [(4-hydroxy-1-methyl-7-phenoxy-isoquinoline-3-carbonyl)-amino]-acetic acid and the pharmaceutically acceptable excipient, and the capsule shell comprises the photostabilizing agent.

In some embodiments, the capsule fill comprises the photostabilizing agent, [(4-hydroxy-1-methyl-7-phenoxy-isoquinoline-3-carbonyl)-amino]-acetic acid, and the pharmaceutically acceptable excipient. In these embodiments, the capsule fill is prepared by mixing (blending) the photostabilizing agent with API and excipients.

In some embodiments, the photostabilizing agent in the capsule comprises titanium dioxide and at least one additional dye selected from the group consisting of Allura Red AC, iron oxide red, iron oxide yellow, and combinations thereof. In another embodiment, the photostabilizing agent comprises iron oxide red and titanium dioxide. In another embodiment, the photostabilizing agent comprises iron oxide red, Allura Red AC, iron oxide yellow, and titanium dioxide. In yet another embodiment, the photostabilizing agent comprises iron oxide red, iron oxide yellow, and titanium dioxide. In still yet another embodiment, the photostabilizing agent comprises Allura Red AC, iron oxide yellow, and titanium dioxide. In still yet another embodiment, the photostabilizing agent comprises iron oxide yellow and titanium dioxide.

Based on the disclosure herein and routine experimentation, one of skill in the art will readily be able to determine the effective amount of photostabilizing agent needed to prevent or reduce the photodegradation of Compound A in the capsule. The amount of photostabilizing agent in the capsule shell can be described as % w/w, percent weight of the photostabilizing agent based on the capsule shell weight. To determine the amount of photostabilizing agent needed to prevent or reduce the photodegradation of Compound A, capsules with capsule shells containing different dyes in different quantities can be tested for photostabilization. As an alternative, the capsule fills containing Compound A can be covered with gelatin films containing different dyes in different quantities, and the photodegradation of Compound A, if any, can be monitored following light exposure (either under ICH condition or sunlight). Example 3 describes several gelatin films with various dye compositions and their photostabilization results.

In one embodiment, the capsule shell comprises from about 1% w/w to about 7% w/w, from about 1.8% w/w to about 6% w/w, from about 2% w/w to about 4% w/w, or from about 2% w/w to about 3.5% w/w photostabilizing agent (based on weight of capsule shell). In another embodiment, the capsule shell comprises from about 1.8% w/w to about 6% w/w photostabilizing agent (based on weight of capsule shell). In another embodiment, the capsule shell comprises from about 2% w/w to about 3.5% w/w photostabilizing agent (based on weight of capsule shell).

In one embodiment, the capsule shell is a gelatin shell. In another embodiment, the capsule shell is a hydroxypropylmethylcellulose (HPMC) shell.

In one embodiment, the capsule shell comprises about 2% w/w iron oxide red and about 0.9% w/w titanium dioxide (based on weight of capsule shell); or about 0.3% w/w Allura Red AC, about 1% w/w iron oxide yellow, and about 1% w/w titanium dioxide (based on weight of capsule shell); or about 0.7% w/w iron oxide red, about 0.3% w/w Allura Red AC, about 1% w/w iron oxide yellow, and about 1% w/w titanium dioxide (based on weight of capsule shell); or about 1% w/w iron oxide red, about 1% w/w iron oxide yellow, and about 1% w/w titanium dioxide (based on weight of capsule shell); or about 1% w/w Allura Red AC, about 1% w/w iron oxide yellow, and about 1% w/w titanium dioxide (based on weight of capsule shell); or about 2% w/w iron oxide red and about 1% w/w titanium dioxide (based on weight of capsule shell); or about 2% w/w iron oxide yellow and about 1% w/w titanium dioxide (based on weight of capsule shell).

In some embodiments, the capsule fill comprises [(4-hydroxy-1-methyl-7-phenoxy-isoquinoline-3-carbonyl)-amino]-acetic acid in an amount from about 1% to about 90% w/w, from about 5% to about 80% w/w, from about 5% to about 40% w/w, from about 8% to about 30% w/w, 10% to about 30% w/w or from about 12% to about 15% w/w (based on the weight of the capsule fill); and a pharmaceutically acceptable excipient.

In some embodiments, the capsule fill comprises about 1 mg to about 400 mg, about 5 mg to about 250 mg, about 20 mg to about 200 mg, about 20 mg to about 100 mg or about 20 mg to about 50 mg of [(4-hydroxy-1-methyl-7-phenoxy-isoquinoline-3-carbonyl)-amino]-acetic acid; and a pharmaceutically acceptable excipient. In other embodiments, the capsule fill comprises about 1 mg, about 5 mg, about 10 mg, about 15 mg, about 20 mg, about 25 mg, about 50 mg, about 75 mg, about 100 mg, about 125 mg, about 150 mg, about 175 mg, about 200 mg, about 250 mg, about 300 mg, about 350 mg, or about 400 mg of [(4-hydroxy-1-methyl-7-phenoxy-isoquinoline-3-carbonyl)-amino]-acetic acid; and a pharmaceutically acceptable excipient. In other embodiments, the capsule fill comprises about 20 mg, or about 50 mg of [(4-hydroxy-1-methyl-7-phenoxy-isoquinoline-3-carbonyl)-amino]-acetic acid; and a pharmaceutically acceptable excipient.

Suitable excipients are, for example, fillers such as sugars, including lactose, lactose monohydrate, sucrose, mannitol, or sorbitol; cellulose preparations such as, for example, maize starch, wheat starch, rice starch, potato starch, gelatin, gum tragacanth, methyl cellulose, hydroxypropylmethylcellulose, carboxymethylcellulose sodium, microcrystalline cellulose and/or polyvinylpyrrolidone (PVP or povidone). If desired, disintegrating agents may be added, such as the cross-linked polyvinyl pyrrolidone, agar, croscarmellose sodium or alginic acid or a salt thereof such as sodium alginate. Also, wetting agents such as sodium dodecyl sulfate or lubricants such as magnesium stearate may be included.

In one embodiment, the pharmaceutically acceptable excipient in the capsule comprises lactose monohydrate, microcrystalline cellulose, povidone, croscarmellose sodium, and magnesium stearate.

The present disclosure provides a capsule comprising a capsule fill and a capsule shell, wherein the capsule fill comprises from about 12% to about 15% w/w [(4-hydroxy-1-methyl-7-phenoxy-isoquinoline-3-carbonyl)-amino]-acetic acid (based on the weight of the capsule fill) and a pharmaceutically acceptable excipient, and wherein the capsule shell comprises an effective amount of a photostabilizing agent. In one embodiment, the pharmaceutically acceptable excipient comprises lactose monohydrate, microcrystalline cellulose, povidone, croscarmellose sodium, and magnesium stearate. In another embodiment, the capsule fill comprises about 20 mg or about 50 mg [(4-hydroxy-1-methyl-7-phenoxy-isoquinoline-3-carbonyl)-amino]-acetic acid. In yet another embodiment, the capsule shell comprises from about 2% w/w to about 3.5% w/w photostabilizing agent (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 2% w/w iron oxide red and about 0.9% w/w titanium dioxide (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 0.3% w/w Allura Red AC, about 1% w/w iron oxide yellow, and about 1% w/w titanium dioxide (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 0.7% w/w iron oxide red, about 0.3% w/w Allura Red AC, about 1% w/w iron oxide yellow, and about 1% w/w titanium dioxide (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 1% w/w iron oxide red, about 1% w/w iron oxide yellow, and about 1% w/w titanium dioxide (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 1% w/w Allura Red AC, about 1% w/w iron oxide yellow, and about 1% w/w titanium dioxide (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 2% w/w iron oxide red, and about 1% w/w titanium dioxide (based on the weight of the capsule shell).

In one embodiment, the capsule fill comprises about 20 mg or about 50 mg of [(4-hydroxy-1-methyl-7-phenoxy-isoquinoline-3-carbonyl)-amino]-acetic acid, and pharmaceutically acceptable excipients comprising lactose monohydrate, microcrystalline cellulose, povidone, croscarmellose sodium, and magnesium stearate; and wherein the capsule shell is a gelatin shell comprising about 2% w/w iron oxide yellow, and about 1% w/w titanium dioxide (based on the weight of the capsule shell).

Routes of Administration

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The pharmaceutical formulation may be administered in a local rather than a systemic manner. For example, pharmaceutical formulation can be delivered via injection or in a targeted drug delivery system, such as a depot or sustained release formulation. In one embodiment, the route of administration is oral. When the pharmaceutical formulation is administered orally, it may be administered as a tablet or a capsule.

The pharmaceutical formulations of the present disclosure may be manufactured by any of the methods well-known in the art, such as by conventional mixing, dissolving, granulating, dragee-making, levigating, emulsifying, encapsulating, entrapping, or lyophilizing processes. As noted above, the compositions can include one or more pharmaceutically acceptable excipients that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In one embodiment of the present disclosure, the pharmaceutical formulations are intended for oral administration. For oral administration, it can be formulated readily by combining Compound A with pharmaceutically acceptable excipients well known in the art. Such excipients enable Compound A to be formulated as tablets, pills, dragees, capsules, liquids, gels, syrups, slurries, suspensions and the like, for oral ingestion by a subject. The pharmaceutical formulation may also be formulated into rectal compositions such as suppositories or retention enemas, e.g., containing conventional suppository bases such as cocoa butter or other glycerides.

Pharmaceutical preparations for oral use can be obtained using solid excipients, optionally grinding a resulting mixture, and processing the mixture of granules, after adding suitable auxiliaries, if desired, to obtain tablets or tablet cores. Suitable excipients are well known in the art and are described elsewhere herein.

Pharmaceutical preparations for oral administration include push-fit capsules made of gelatin, HPMC, and other suitable materials, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added.

The pharmaceutical formulations may also be formulated as a depot preparation. Such long acting formulations may be administered by implantation (for example, subcutaneously or intramuscularly) or by intramuscular injection. Thus, for example, the pharmaceutical formulations may be formulated with suitable polymeric or hydrophobic materials (for example as an emulsion in an acceptable oil) or ion exchange resins, or as sparingly soluble derivatives, for example, as a sparingly soluble salt.

For any composition used in the various treatments embodied herein, an effective dose (or therapeutically effective dose) can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and non-human animal studies. In one embodiment, the dosage may be from 0.05 mg/kg to about 700 mg/kg. Typically, the dosage may be from about 0.05 mg/kg to about 500 mg/kg; from about 0.1 mg/kg to about 250 mg/kg; from about 0.2 mg/kg to about 100 mg/kg; from about 0.3 mg/kg to about 10 mg/kg; from about 0.5 mg/kg to about 5 mg/kg; or from about 1 mg/kg to about 2 mg/kg. For example, the dosage may be about 0.5 mg/kg; about 0.7 mg/kg; 1.0 mg/kg; about 1.2 mg/kg; about 1.5 mg/kg; about 2.0 mg/kg; about 2.5 mg/kg; about 3.0 mg/kg; about 3.5 mg/kg; about 4.0 mg/kg; about 4.5 mg/kg; or about 5.0 mg/kg. The dosages may be administered at various intervals, for example, every day, every other day, 1, 2, or 3 times a week, etc. Typically, the dosages is administered 2 or 3 times a week.

A therapeutically effective dose of a compound refers to that amount of the compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Compounds that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate a desired parameter, e.g., endogenous erythropoietin plasma levels, i.e. minimal effective concentration (MEC). The MEC will vary for each compound but can be estimated from, for example, in vitro data. In cases of local administration or selective uptake, the effective local concentration of the drug may not be related to plasma concentration. Alternatively, modulation of a desired parameter, e.g., stimulation of endogenous erythropoietin, may be achieved by 1) administering a loading dose followed by a maintenance dose, 2) administering an induction dose to rapidly achieve the desired parameter, e.g., erythropoietin levels, within a target range, followed by a lower maintenance dose to maintain, e.g., hematocrit, within a desired target range, or 3) repeated intermittent dosing.

The amount of compound or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Pharmaceutical formulations of the disclosure formulated in a compatible pharmaceutical excipient may also be prepared, placed in an appropriate container, and labeled for treatment of an indicated condition. Suitable conditions indicated on the label may include treatment of conditions, disorders, or diseases in which anemia is a major indication.

Methods

The present disclosure provides a method of inhibiting (preventing and/or reducing) the photodegradation of [(4-hydroxy-1-methyl-7-phenoxy-isoquinoline-3-carbonyl)-amino]-acetic acid (Compound A). In one embodiment, the method comprises formulating [(4-hydroxy-1-methyl-7-phenoxy-isoquinoline-3-carbonyl)-amino]-acetic acid with an effective amount of a photostabilizing agent. An effective amount of photostabilizing agent is the amount sufficient to limit the amount of photodegradation product of Compound A that is produced to a level that is less than about 0.2% w/w Compound A (or 2000 ppm), under ICH conditions. In one embodiment, the photostabilizing agent comprises titanium dioxide. In one embodiment, the photostabilizing agent comprises a dye. In some embodiments, the method comprises formulating [(4-hydroxy-1-methyl-7-phenoxy-isoquinoline-3-carbonyl)-amino]-acetic acid with titanium dioxide and at least one additional dye. In a further embodiment, the photostabilizing agent blocks light at a wavelength range of between about 220 and about 550 nm. In other embodiments, the dye is selected from the group consisting of a black dye, a blue dye, a green dye, a red dye, an orange dye, a yellow dye, and combinations thereof. In another embodiment, the dye is selected from the group consisting of a red dye, an orange dye, a yellow dye, and combinations thereof. The present invention further provides a method of inhibiting (preventing and/or reducing) the photodegradation of [(4-hydroxy-1-methyl-7-phenoxy-isoquinoline-3-carbonyl)-amino]-acetic acid (Compound A), the method comprising formulating [(4-hydroxy-1-methyl-7-phenoxy-isoquinoline-3-carbonyl)-amino]-acetic acid with an effective amount of a photostabilizing agent, and a pharmaceutically acceptable excipient. Various formulations comprising photostabilizing agents have been described herein.

Compound A can be formulated with the photostabilizing agent in any conventional manner, for example, by mixing or blending Compound A and photostabilizing agent together into a homogeneous dry powder, compressing into solid tablet forms, filling into capsules, etc. Alternatively, Compound A can be formulated with the photostabilizing agent by coating a tablet core comprising Compound A with a coating comprising the photostabilizing agent, or by enclosing a capsule fill comprising Compound A within a capsule shell comprising the photostabilizing agent.

In other embodiments, the method of inhibiting the photodegradation of Compound A can be achieved with photostabilizing packaging, either as an alternative, or as an addition to the photostabilizing formulation. Examples of photostabilizing packaging for tablets or capsules include, but are not limited to, opaque containers or wrappings such as, a brown bottle, a black-lined bottle, an amber vial, an opaque blister pack, a blister pack made from a blister film containing a photostabilizing agent, and a foil-lined packaging.

One aspect of the disclosure provides for use of the pharmaceutical formulations for the manufacture of a medicament for use in treating various conditions or disorders as described herein. It also provides methods of using the pharmaceutical formulation or composition or medicament thereof, to treat, pretreat, or delay progression or onset of various conditions or disorders as described herein.

The medicaments or compositions can be used to modulate the stability and/or activity of HIF, and thereby activate HIF-regulated gene expression. In one aspect, the medicaments or compositions can be used to inhibit or reduce the activity of a HIF hydroxylase enzyme, particularly a HIF prolyl hydroxylase enzyme, for example, EGLN1, EGLN2, and EGLN3 (also known as PHD2, PHD1 and PHD3, respectively), described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340).

The pharmaceutical formulations described herein can be used in methods to treat, pretreat, or delay progression or onset of conditions associated with HIF including, but not limited to, anemic, ischemic, and hypoxic conditions. In various embodiments, the pharmaceutical formulation is administered immediately following a condition producing acute ischemia, e.g., myocardial infarction, pulmonary embolism, intestinal infarction, ischemic stroke, and renal ischemic-reperfusion injury. In another embodiment, pharmaceutical formulation is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, pharmaceutical formulation is administered immediately after a trauma or injury. In other embodiments, pharmaceutical formulation can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, pharmaceutical formulation may be administered to pretreat a subject to decrease or prevent the development of tissue damage associated with ischemia or hypoxia. In other embodiments, the pharmaceutical formulations and compositions can be used in a method to treat or delay progression of inflammatory bowel disease, including various forms of colitis (e.g., ulcerative colitis) and Crohn's disease.

The pharmaceutical formulations and compositions can be used in a method to treat anemia, to increase blood hemoglobin levels, and/or to increase hematocrit, in a subject in need thereof. In one aspect, the pharmaceutical formulations and compositions can be used in a method to treat anemia, to increase blood hemoglobin levels, and/or to increase hematocrit, in a subject with chronic kidney disease or end stage renal disorder. In one aspect, the pharmaceutical formulations and compositions can be used in a method to treat anemia, to increase blood hemoglobin levels, and/or to increase hematocrit, in a subject having anemia of chronic disease.

The pharmaceutical formulations and compositions can also be used in a method for regulating glucose metabolism and achieving glucose homeostasis. Methods for decreasing blood glucose levels, reducing insulin resistance, decreasing glycated hemoglobin levels, decreasing blood triglyceride levels, and improving glycemic control in a subject are also accomplished by administering the formulations or compositions described herein. Methods for treating or preventing diabetes, hyperglycemia, and other conditions associated with increased blood glucose levels are provided, as are methods for treating or preventing conditions associated with diabetes, e.g., conditions that are risk factors for or that develop in parallel with or as a result of diabetes.

The pharmaceutical formulation can also be used to increase endogenous erythropoietin (EPO). The pharmaceutical formulation can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

In one aspect, the pharmaceutical formulations and compositions can be used in a method for inducing enhanced or complete erythropoiesis in a subject.

The disclosure is also directed to use of a pharmaceutical formulation to treat, pretreat, or delay onset of a condition associated with a disorder selected from the group consisting of anemic disorders; neurological disorders and/or injuries including cases of stroke, trauma, epilepsy, and neurodegenerative disease; cardiac ischemia including, but not limited to, myocardial infarction and congestive heart failure; liver ischemia including, but not limited to, cardiac cirrhosis; renal ischemia including, but not limited to, acute kidney failure and chronic kidney failure; peripheral vascular disorders, ulcers, burns, and chronic wounds; pulmonary embolism; and ischemic-reperfusion injury. In one aspect the formulations and compositions are useful in a method for treating multiple sclerosis and/or increasing neurogenesis.

In a further aspect, the formulations and compositions can be used in a method for reducing blood pressure or preventing an increase in blood pressure and for treating or preventing hypertension or prehypertension in any subject, including, but not limited to, subjects having kidney disease.

In another embodiment, the present invention provides use for the formulations and compositions in a method for improving kidney function in a subject having or at risk for having impaired kidney function, the method comprising administering to the subject an agent that inhibits hypoxia inducible factor (HIF) hydroxylase activity.

In another aspect, the formulations and compositions can be used in a method for regulation of iron processing and treatment/prevention of conditions associated with deficiencies in iron and/or iron processing. In certain aspects, the invention contemplates use of the formulations and compositions in methods for increasing serum iron, increasing transferrin saturation, increasing soluble transferrin receptor levels, and increasing serum ferritin levels in a subject.

In another aspect, the formulations and compositions can be used in methods for treatment of high cholesterol by reducing the circulating level of total cholesterol and particularly by reducing the circulating level of low density lipoprotein cholesterol and/or very low density lipoprotein cholesterol, and/or increasing the ratio of high density lipoprotein cholesterol/low density protein cholesterol.

Methods of using HIF prolyl hydroxylase inhibitors, and in particular, Compound A, to treat various conditions and disorders have been described in numerous publications including, U.S. Patent Application Publication Nos. 2003/0176317, 2003/0153503, 2004/0204356, 2004/0235082, 2005/0020487, 2007/0042937, 2007/0004627, 2006/0276477, 2007/0293575, 2012/0149712, 2007/0259960, 2007/0292433, 2011/0039878, 2011/0039885, 2010/0144737, 2011/0039879, and 2011/0263642; PCT Publication No. WO2012/097329, WO2012/097331, and WO2013/070908; International Patent Application No. PCT/US2013/029851.

The disclosure is also directed to a method of inhibiting the activity of at least one hydroxylase enzyme which modifies the alpha subunit of hypoxia inducible factor. The HIF hydroxylase enzyme may be a prolyl hydroxylase including, but not limited to, the group consisting of EGLN1, EGLN2, and EGLN3 (also known as PHD2, PHD1 and PHD3, respectively), described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). The method comprises contacting the enzyme with Compound A. In some embodiments, the HIF hydroxylase enzyme is an asparaginyl hydroxylase or a prolyl hydroxylase. In other embodiments, the HIF hydroxylase enzyme is a factor inhibiting HIF, human EGLN1, EGLN2, or EGLN3.

While this disclosure has been described in conjunction with specific embodiments and examples, it will be apparent to a person of ordinary skill in the art, having regard to that skill and this disclosure, that equivalents of the specifically disclosed materials and methods will also be applicable to this disclosure; and such equivalents are intended to be included within the following claims.

EXAMPLES

Example 1. Solid State Sunlight Exposure of Compound A

Approximately 500 mg of Compound A dry powder was placed in a 1-gallon polyethylene bag and exposed to sunlight for two months consecutively during daylight hours. The powder was in a very thin layer and the bag was shaken often to ensure that all the powder and not just the top layer was exposed to sunlight. A control sample of Compound A powder was stored in an amber vial in the dark for the same amount of time for comparison purposes. After two months, visual inspection of the two samples indicated that the light-exposed sample had become off-white, compared to the control sample which was yellow. The light-exposed sample and the control sample were analyzed by HPLC to evaluate differences in their composition. The HPLC method used a reverse phase Zorbax Eclipse XDB-$C_8$, 3.5 µm, 4.6×150 mm column. The mobile phase was comprised of water and acetonitrile mixtures acidified with trifluoroacetic acid. Gradient elution with increasing acetonitrile provided chromatograms of the control sample of Compound A (FIG. 1, before light exposure) and the light-exposed sample of Compound A (FIG. 1, after light exposure) with UV detection at 230 nm. The HPLC of the light-exposed sample shows the appearance of a new peak, designated as "Photodegradation Product" in FIG. 1.

Before exposure to sunlight, the Compound A powder had a purity value of 99.1% as measured by reverse phase HPLC and no single impurity was present at a level above 0.2% w/w (2000 ppm). After exposure to sunlight, the Compound A powder had a slightly lower purity value of 98.4%. After exposure to sunlight, a new peak appeared in the chromatogram evidencing a new molecule. The new peak had an area of 0.34%. The fact that the area percent of Compound A decreased on exposure to sunlight and the new molecule appeared suggests that a fraction of Compound A is converting to the new molecule, a photodegradation product.

Example 2. Photostabilizing Coating of Tablet

It was found that tablets comprising [(4-hydroxy-1-methyl-7-phenoxy-isoquinoline-3-carbonyl)-amino]-acetic acid photodegrade upon exposure to light. To reduce the photodegradation of Compound A in the tablets, various coatings were tested for their photostabilizing properties.

Pink/Peach coating formulas tested included a coating comprising
Formula 1: iron oxide red, iron oxide yellow and titanium dioxide ("Pink/Peach #1");
Formula 2: Sunset Yellow FCF, iron oxide red and titanium dioxide ("Pink/Peach #2"); or
Formula 3: iron oxide red, iron oxide yellow and titanium dioxide ("Pink/Peach #3").

The red coating formulas tested included a coating comprising

Formula 4: Allura Red AC and Indigotine aluminum lakes, and titanium dioxide ("Allura Red AC/Indigotine");

Formula 5: Allura Red AC aluminum lake and titanium dioxide ("Allura Red AC"); or Formula 6: Iron oxide red and titanium dioxide ("Red Iron Oxide").

Tablets comprising either 20 mg or 100 mg of [(4-hydroxy-1-methyl-7-phenoxy-isoquinoline-3-carbonyl)-amino]-acetic acid were coated in an evenly distributed layer with different amounts of photo stabilizing agent per tablet surface area ($mg/cm^2$) in a coating pan with reduced lighting. Table 1 lists examples of tablet coatings at various levels using different coating formulas. The 3%, 4%, 4.5% or 7.5% coating level is the percentage of the weight of the coating material over the weight of the tablet core being coated.

TABLE 1

Examples of Photostabilizing Agents per Tablet Surface Area Present in Tablets Coated at Different Coating Levels 20 mg strength tablet with 3% target coating level

| | Formula 1a | Formula 2a | Formula 3a | Formula 4a | Formula 5a | Formula 6a |
|---|---|---|---|---|---|---|
| Total Allura Red AC ($mg/cm^2$) | 0.000 | 0.000 | 0.000 | 0.136 | 0.123 | 0.000 |
| Total Indigotine ($mg/cm^2$) | 0.000 | 0.000 | 0.000 | 0.0005 | 0.000 | 0.000 |
| Total Sunset Yellow FCF ($mg/cm^2$) | 0.000 | 0.009 | 0.000 | 0.000 | 0.000 | 0.000 |
| Red iron oxide ($mg/cm^2$) | 0.008 | 0.003 | 0.005 | 0.000 | 0.000 | 0.134 |
| Yellow iron oxide ($mg/cm^2$) | 0.043 | 0.000 | 0.005 | 0.000 | 0.000 | 0.000 |
| Titanium dioxide ($mg/cm^2$) | 0.621 | 0.609 | 0.661 | 0.126 | 0.125 | 0.639 |

20 mg strength tablet with 4% target coating level

| | Formula 1b | Formula 2b | Formula 3b | Formula 4b | Formula 5b | Formula 6b |
|---|---|---|---|---|---|---|
| Total Allura Red AC ($mg/cm^2$) | 0.000 | 0.000 | 0.000 | 0.182 | 0.163 | 0.000 |
| Total Indigotine ($mg/cm^2$) | 0.000 | 0.000 | 0.000 | 0.001 | 0.000 | 0.000 |
| Total Sunset Yellow FCF ($mg/cm^2$) | 0.000 | 0.012 | 0.000 | 0.000 | 0.000 | 0.000 |
| Red iron oxide ($mg/cm^2$) | 0.010 | 0.004 | 0.007 | 0.000 | 0.000 | 0.179 |
| Yellow iron oxide ($mg/cm^2$) | 0.057 | 0.000 | 0.007 | 0.000 | 0.000 | 0.000 |
| Titanium dioxide ($mg/cm^2$) | 0.828 | 0.811 | 0.881 | 0.168 | 0.167 | 0.852 |

20 mg strength tablet with 7.5% target coating level

| | Formula 1c | Formula 2c | Formula 3c | Formula 4c | Formula 5c | Formula 6c |
|---|---|---|---|---|---|---|
| Total Allura Red AC ($mg/cm^2$) | 0.000 | 0.000 | 0.000 | 0.341 | 0.306 | 0.000 |
| Total Indigotine ($mg/cm^2$) | 0.000 | 0.000 | 0.000 | 0.001 | 0.000 | 0.000 |
| Total Sunset Yellow FCF ($mg/cm^2$) | 0.000 | 0.023 | 0.000 | 0.000 | 0.000 | 0.000 |
| Red iron oxide ($mg/cm^2$) | 0.019 | 0.007 | 0.013 | 0.000 | 0.000 | 0.336 |
| Yellow iron oxide ($mg/cm^2$) | 0.107 | 0.000 | 0.013 | 0.000 | 0.000 | 0.000 |
| Titanium dioxide ($mg/cm^2$) | 1.552 | 1.521 | 1.652 | 0.316 | 0.314 | 1.598 |

100 mg strength tablet with 3% target coating level

| | Formula 1d | Formula 2d | Formula 3d | Formula 4d | Formula 5d | Formula 6d |
|---|---|---|---|---|---|---|
| Total Allura Red AC ($mg/cm^2$) | 0.000 | 0.000 | 0.000 | 0.240 | 0.216 | 0.000 |
| Total Indigotine ($mg/cm^2$) | 0.000 | 0.000 | 0.000 | 0.001 | 0.000 | 0.000 |
| Total Sunset Yellow FCF ($mg/cm^2$) | 0.000 | 0.016 | 0.000 | 0.000 | 0.000 | 0.000 |
| Red iron oxide ($mg/cm^2$) | 0.014 | 0.005 | 0.009 | 0.000 | 0.000 | 0.237 |
| Yellow iron oxide ($mg/cm^2$) | 0.075 | 0.000 | 0.009 | 0.000 | 0.000 | 0.000 |
| Titanium dioxide ($mg/cm^2$) | 1.094 | 1.073 | 1.165 | 0.222 | 0.221 | 1.127 |

100 mg strength tablet with 4% target coating level

| | Formula 1e | Formula 2e | Formula 3e | Formula 4e | Formula 5e | Formula 6e |
|---|---|---|---|---|---|---|
| Total Allura Red AC ($mg/cm^2$) | 0.000 | 0.000 | 0.000 | 0.320 | 0.288 | 0.000 |
| Total Indigotine ($mg/cm^2$) | 0.000 | 0.000 | 0.000 | 0.001 | 0.000 | 0.000 |
| Total Sunset Yellow FCF ($mg/cm^2$) | 0.000 | 0.021 | 0.000 | 0.000 | 0.000 | 0.000 |
| Red iron oxide ($mg/cm^2$) | 0.018 | 0.006 | 0.013 | 0.000 | 0.000 | 0.316 |
| Yellow iron oxide ($mg/cm^2$) | 0.100 | 0.000 | 0.013 | 0.000 | 0.000 | 0.000 |
| Titanium dioxide ($mg/cm^2$) | 1.459 | 1.430 | 1.553 | 0.297 | 0.295 | 1.502 |

TABLE 1-continued

Examples of Photostabilizing Agents per Tablet Surface Area Present in Tablets Coated at Different Coating Levels 100 mg strength tablet with 4.5% target coating level

|  | Formula 1f | Formula 2f | Formula 3f | Formula 4f | Formula 5f | Formula 6f |
|---|---|---|---|---|---|---|
| Total Allura Red AC (mg/cm$^2$) | 0.000 | 0.000 | 0.000 | 0.360 | 0.324 | 0.000 |
| Total Indigotine (mg/cm$^2$) | 0.000 | 0.000 | 0.000 | 0.001 | 0.000 | 0.000 |
| Total Sunset Yellow FCF (mg/cm$^2$) | 0.000 | 0.024 | 0.000 | 0.000 | 0.000 | 0.000 |
| Red iron oxide (mg/cm$^2$) | 0.021 | 0.007 | 0.014 | 0.000 | 0.000 | 0.355 |
| Yellow iron oxide (mg/cm$^2$) | 0.113 | 0.000 | 0.014 | 0.000 | 0.000 | 0.000 |
| Titanium dioxide (mg/cm$^2$) | 1.642 | 1.609 | 1.747 | 0.334 | 0.332 | 1.690 |

The coated tablets were exposed to light (ICH Option 2), and tested for photodegradation by measuring the amount of photodegradation product that was present by using reverse phase HPLC. Dark controls were wrapped in aluminum foil. The reverse phase HPLC method used to quantify photodegradation product had an upper quantitation limit of 0.25% or 2500 ppm. Where values above 0.25% or 2500 ppm were reported, a modified reverse phase HPLC method with a higher upper quantitation limit, but of lower sensitivity, was used. Tables 2 and 3 show mean values (n=10) of photodegradation product (in ppm relative to Compound A) for each red-coated tablet batch tested. "ND" refers to not determined. "NA" refers to not applicable.

TABLE 2

Photodegradation of 20 mg Strength Tablet with Red Coatings

| Coating Formula | | Coating Level (w/w) | Light Exposure | Photodegradation Product Mean Value (ppm) |
|---|---|---|---|---|
| Allura Red AC/ Indigotine | Formula 4a | 3% | ICH Option 2 | 1645 |
| | Formula 4b | 4% | ICH Option 2 | 859 |
| Allura Red AC | Formula 5a | 3% | ICH Option 2 | 1816 |
| | Formula 5b | 4% | ICH Option 2 | 859 |
| Red Iron Oxide | Formula 6a | 3% | ICH Option 2 | 1304 |
| | | | Dark Control | 2 |
| | Formula 6b | 4% | ICH Option 2 | 422 |
| Uncoated | | NA | Dark Control | <2 |
| | | N/A | ICH Option 2 | 5813 |

TABLE 3

Photodegradation of 100 mg Strength Tablet with Red Coatings

| Coating Formula | | Coating Level (w/w) | Light Exposure | Photodegradation Product Mean Value (ppm) |
|---|---|---|---|---|
| Allura Red AC/ Indigotine | Formula 4d | 3% | ICH Option 2 | 241 |
| | Formula 4e | 4% | ICH Option 2 | 68 |
| Allura Red AC | Formula 5d | 3% | ICH Option 2 | 151 |
| | Formula 5e | 4% | ICH Option 2 | 37 |
| Red Iron Oxide | Formula 6d | 3% | ICH Option 2 | 52 |
| | Formula 6e | 4% | ICH Option 2 | 8 |
| Uncoated | | N/A | ICH Option 2 | 2962 |

Figure 2A:
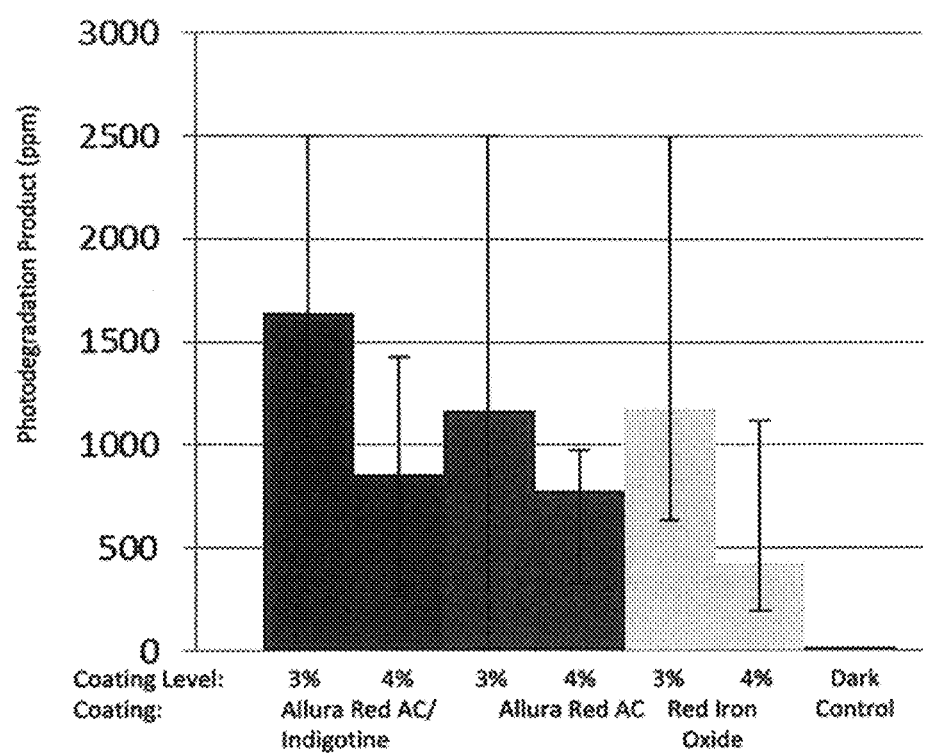
FIGS. 2A and 2B illustrates the amount of photodegradation product in tablets containing either 20 mg (FIG. 2A) or 100 mg (FIG. 2B) of Compound A upon light exposure. The tablets are coated with a coating formula containing Allura Red AC/Indigotine/titanium dioxide (labeled as Allura Red AC/Indigotine in figures), Allura Red AC/titanium dioxide (labeled as Allura Red AC in figures), or red iron oxide/titanium dioxide (labeled as Red Iron Oxide in figures). See Example 2 for details.
Figure 2B:
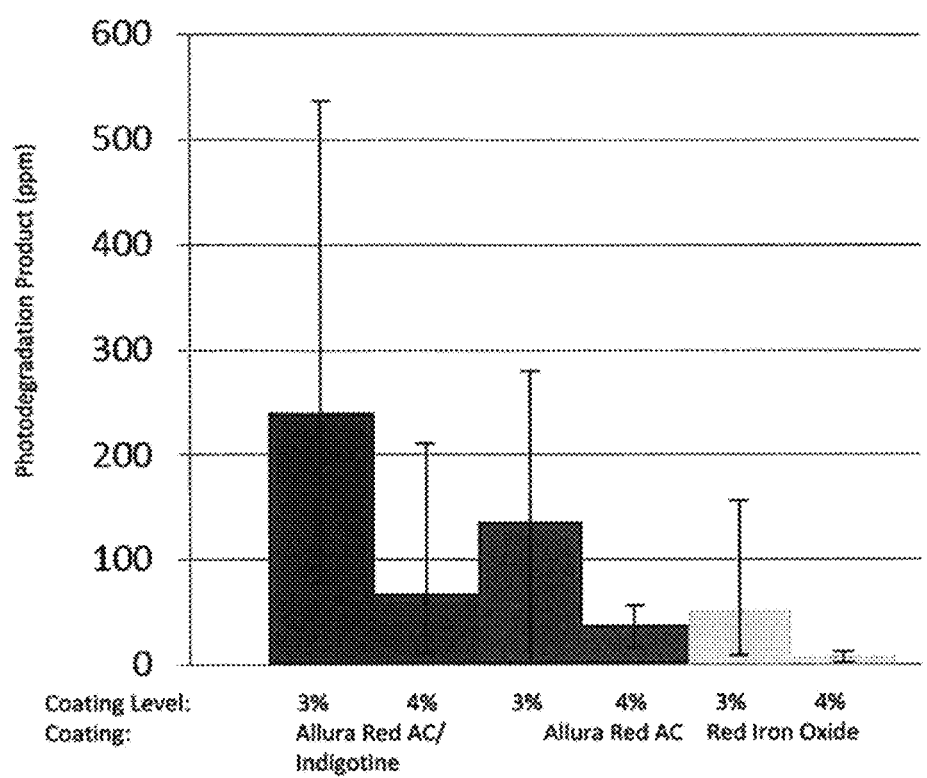

These results are depicted graphically in FIGS. 2A (20 mg strength tablet) and 2B (100 mg strength tablet).

Figure 3A:
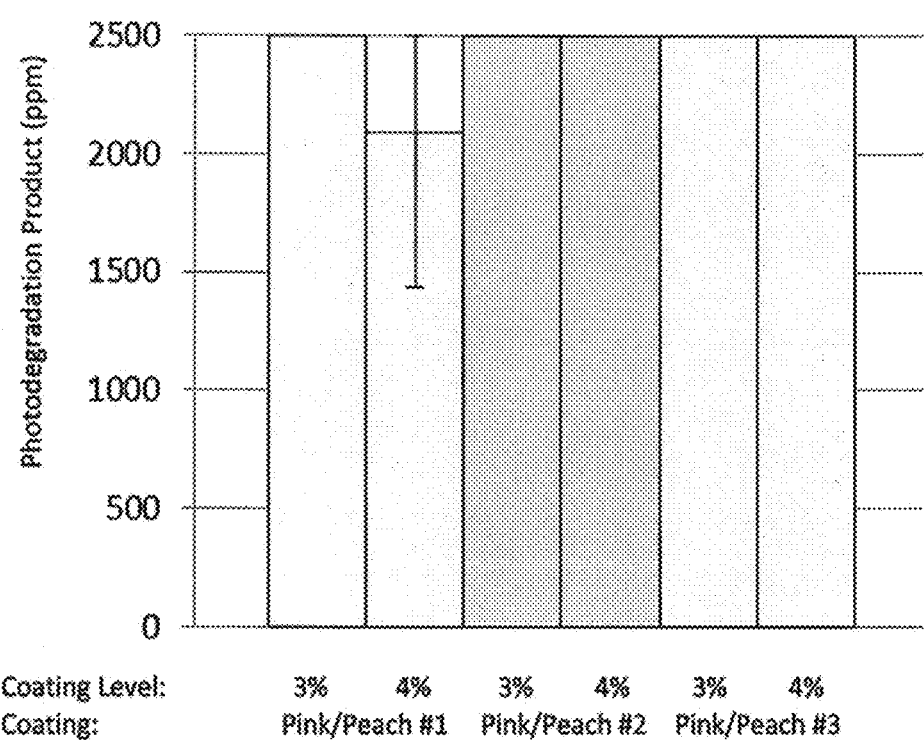
FIGS. 3A and 3B illustrates the amount of photodegradation product in tablets containing either 20 mg (FIG. 3A) or 100 mg (FIG. 3B) of Compound A upon light exposure. The tablets are coated with a variety of pink/peach coating formulas. See Example 2 for details.
Figure 3B:
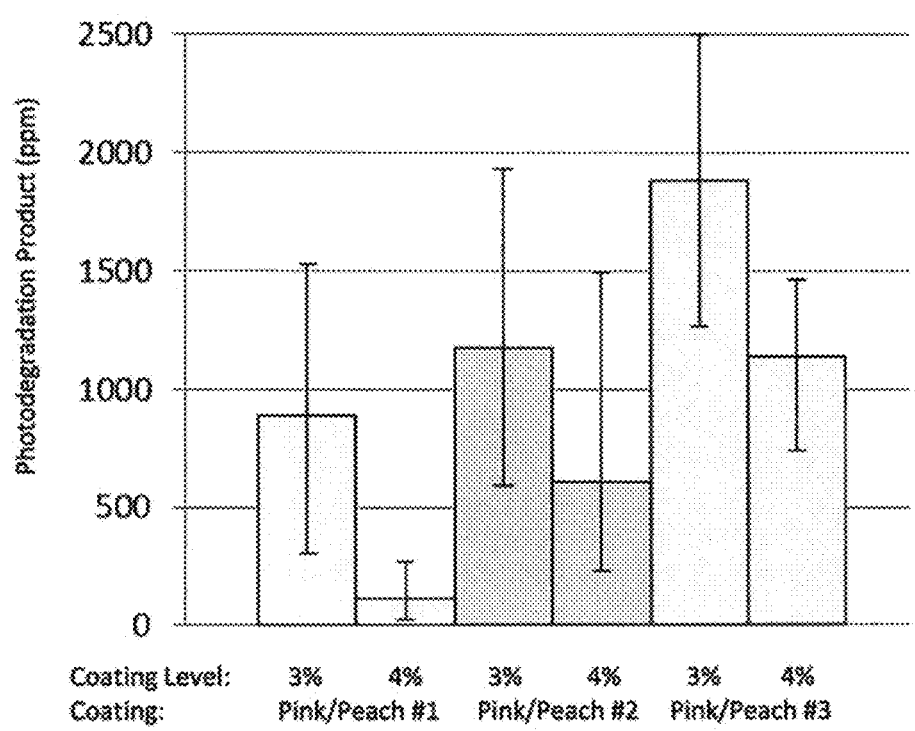

Photodegradation results for tablets coated with pink/peach formulas at the 3% or 4% coating level (based on the weight of the tablet core), after exposure to ICH Option 2 conditions are shown in FIG. 3A and Table 4 for the 20 mg strength tablets, and in FIG. 3B and Table 5 for the 100 mg strength tablets.

TABLE 4

Photodegradation of 20 mg Strength Tablet with Pink/Peach Coatings

| Coating Formula | | Coating Level (w/w) | Light Exposure | Photodegradation Product Mean (ppm) |
|---|---|---|---|---|
| Pink/Peach #1 | Formula 1a | 3% | ICH Option 2 | ≥2500 |
| | | | Dark Control | 2 |
| | Formula 1b | 4% | ICH Option 2 | 2079 |
| Pink/Peach #2 | Formula 2a | 3% | ICH Option 2 | ≥2500 |
| | Formula 2b | 4% | ICH Option 2 | ≥2500 |
| Pink/Peach #3 | Formula 3a | 3% | ICH Option 2 | >2500 |
| | Formula 3b | 4% | ICH Option 2 | ≥2500 |

TABLE 5

Photodegradation of 100 mg Strength Tablet with Pink/Peach Coatings

| Coating Formula | | Coating Level (w/w) | Light Exposure | Photodegradation Product Mean (ppm) |
|---|---|---|---|---|
| Pink/Peach #1 | Formula 1d | 3% | ICH Option 2 | 889 |
| | Formula 1e | 4% | ICH Option 2 | 115 |
| Pink/Peach #2 | Formula 2d | 3% | ICH Option 2 | 1173 |
| | Formula 2e | 4% | ICH Option 2 | 608 |
| Pink/Peach #3 | Formula 3d | 3% | ICH Option 2 | 1885 |
| | Formula 3e | 4% | ICH Option 2 | 1138 |

Example 3. Photostabilizing Gelatin Capsule

Compound A in gelatin capsules also exhibits photodegradation upon light exposure. Gelatin film coatings containing various dye combinations were tested for their photostabilizing properties.

Gelatin capsules comprising [(4-hydroxy-1-methyl-7-phenoxy-isoquinoline-3-carbonyl)-amino]-acetic acid in colorless transparent hard gelatin capsule shells were covered with a gelatin film comprising various photostabilizing agents, exposed to light under ICH Option 2 described herein, and tested for photodegradation of [(4-hydroxy-1-methyl-7-phenoxy-isoquinoline-3-carbonyl)-amino]-acetic acid by measuring the amount of photodegradation product using reverse phase HPLC described in Example 1. Results represent the mean value of photodegradation product measured in 10 capsules.

The composition of the hard gelatin films tested is shown in Table 6 below.

TABLE 6

Gelatin Films

| Ingredient | | % w/w (based on weight of capsule shell) |
|---|---|---|
| Orange #1 | Yellow iron oxide | 1% |
| | Allura Red AC | 0.3% |
| | Titanium dioxide | 1% |
| Orange #2 | Yellow iron oxide | 1% |
| | Red iron oxide | 0.7% |
| | Allura Red AC | 0.3% |
| | Titanium dioxide | 1% |
| Orange #3 | Yellow iron oxide | 1% |
| | Red iron oxide | 1% |
| | Titanium dioxide | 1% |
| Red #1 | Red iron oxide | 2% |
| | Titanium dioxide | 1% |
| Yellow | Yellow iron oxide | 2% |
| | Titanium dioxide | 1% |
| Orange #4 | Yellow iron oxide | 1% |
| | Allura Red AC | 1% |
| | Titanium dioxide | 1% |
| Blue | Indigotine | 1% |
| | Titanium dioxide | 1% |
| Red #2 | Red iron oxide | 2% |
| | Titanium dioxide | 0.9% |

Figure 4:
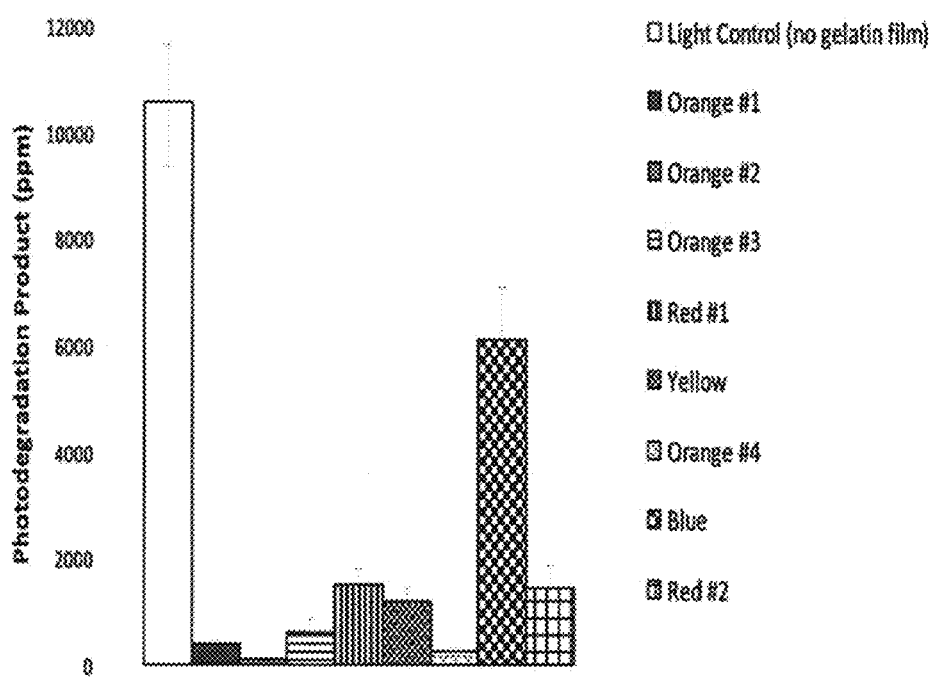
FIG. 4 demonstrates the amount of photodegradation product in capsules covered with gelatin films containing various photostabilizing agents upon light exposure. See Example 3 for details.

As shown in Table 7 and FIG. 4, the orange dyes offered the best photostabilization of Compound A in the hard gelatin capsules.

TABLE 7

Photodegradation of Hard Gelatin Capsules Containing Compound A

| Gelatin Film | Photodegradation Product Mean (ppm) |
|---|---|
| Light Control (No Gelatin Film) | 10563 |
| Orange #1 | 378 |
| Orange #2 | 96 |
| Orange #3 | 619 |
| Red #1 | 1500 |
| Yellow | 1194 |
| Orange #4 | 247 |
| Blue | 6100 |
| Red #2 | 1432 |

What is claimed is:

1. A tablet comprising a tablet core and a coating, wherein the tablet core comprises [(4-hydroxy-1-methyl-7-phenoxy-isoquinoline-3-carbonyl)-amino]-acetic acid, and the coating comprises a photostabilizing agent, wherein the photostabilizing agent:

i) consists essentially of from about 0.1 to about 2 mg/cm$^2$ titanium dioxide and from about 0.1 to about 0.4 mg/cm$^2$ Allura Red AC or from about 0.1 to about 0.4 mg/cm$^2$ Allura Red AC in aluminum lake; and optionally at least one additional dye selected from the group consisting of:

from about 0.004 to about 0.4 mg/cm$^2$ iron oxide red;

from about 0.009 to about 0.2 mg/cm$^2$ iron oxide yellow;

from about 0.01 to about 0.03 mg/cm$^2$ Sunset Yellow FCF; and from about 0.01 to about 0.03 mg/cm$^2$ Sunset Yellow FCF in aluminum lake;

wherein the amount of photostabilizing agent is based on surface area of the tablet core; and ii) prevents the transmission of light at a wavelength range of between about 200 nm and 550 nm and further wherein the tablet contains less than about 0.2% w/w photodegradation product of [(4-hydroxy-1-methyl-7-phenoxy-isoquinoline-3-carbonyl)-amino]-acetic acid relative to the amount of [(4-hydroxy-1-methyl-7-phenoxy-isoquinoline-3-carbonyl)-amino]-acetic acid.

2. The tablet of claim 1, comprising from about 20 mg to about 200 mg of [(4-hydroxy-1-methyl-7-phenoxy-isoquinoline-3-carbonyl)-amino]-acetic acid.

3. The tablet of claim 1, comprising about 20 mg, about 50 mg, or about 100 mg of [(4-hydroxy-1-methyl-7-phenoxy-isoquinoline-3-carbonyl)-amino]-acetic acid.

4. The tablet of claim 1, wherein the tablet comprises a tablet core and a coating and the tablet core comprises [(4-hydroxy-1-methyl-7-phenoxy-isoquinoline-3-carbonyl)-amino]-acetic acid, and the coating comprises the photostabilizing agent, and the coating is present in an amount from about 3% to about 8% w/w based on the weight of the tablet core.

5. The tablet of claim 4, wherein the coating comprises from about 0.1 to about 0.4 mg/cm$^2$ titanium dioxide and from about 0.1 to about 0.4 mg/cm$^2$ Allura Red AC in aluminum lake, and wherein the amount of titanium dioxide and Allura Red AC in aluminum lake is based on surface area of the tablet core.

6. The tablet of claim 5, wherein the tablet core comprises about 20 mg, about 50 mg or about 100 mg of [(4-hydroxy-1-methyl-7-phenoxy-isoquinoline-3-carbonyl)-amino]-acetic acid, lactose monohydrate, microcrystalline cellulose, povidone, croscarmellose sodium, and magnesium stearate; and wherein the photostabilizing agent comprises 0.1 to about 0.4 mg/cm$^2$ titanium dioxide and from about 0.1 to about 0.4 mg/cm$^2$ Allura Red AC in aluminum lake wherein the amount of titanium dioxide and Allura Red AC in aluminum lake is based on surface area of the tablet core.

* * * * *